US006110465A

United States Patent [19]

Bukh et al.

[11] Patent Number: 6,110,465

[45] Date of Patent: Aug. 29, 2000

[54] NUCLEOTIDE AND DEDUCED AMINO ACID SEQUENCES OF HYPERVARIABLE REGION 1 OF THE ENVELOPE 2 GENE OF ISOLATES OF HEPATITIS C VIRUS AND THE USE OF REAGENTS DERIVED FROM THESE HYPERVARIABLE SEQUENCES IN DIAGNOSTIC METHODS AND VACCINES

[75] Inventors: Jens Bukh, Bethesda; Roger H. Miller, Rockville; Robert H. Purcell, Boyds, all of Md.

[73] Assignee: The United States of America as represented by the Department of Health and Human Services, Washington, D.C.

[21] Appl. No.: 08/484,322

[22] Filed: Jun. 7, 1995

[51] Int. Cl.$^7$ .................. A61K 39/29

[52] U.S. Cl. .................. 424/189.1; 424/186.1; 424/187.1; 424/193.1; 424/278.1; 424/228.1; 435/69.3; 435/252.3; 435/320.1; 530/324; 530/325; 530/26; 530/327; 530/328; 530/329

[58] Field of Search .................. 435/69.3, 172.1, 435/172.3, 252.3, 320.1; 530/324–329, 350; 424/185.1, 186.1, 189.1, 193.1, 199.1, 278.1, 228.1

[56] References Cited

FOREIGN PATENT DOCUMENTS

| | | |
|---|---|---|
| 0 468 527 A2 | 2/1992 | European Pat. Off. . |
| WO 94/26306 | 11/1993 | European Pat. Off. . |
| 0 726 463 A3 | 11/1996 | European Pat. Off. . |
| WO 93/06126 | 4/1993 | WIPO . |
| WO 93/18054 | 9/1993 | WIPO . |

OTHER PUBLICATIONS

Choo, et al., "Vaccination of chimpanzees against infection by the hepatitis C virus," *Proc. Natl. Acad. Sci. USA*, (1994) 91:1294–1298.

Bukh, J., et al., "Sequence analysis of the core gene of 14 hepatitis C virus genotypes," *Proc. Natl. Acad. Sci. USA*, (1994) 91:8239–8243.

Bukh, J., et al., "At least 12 genotypes of hepatitis C virus predicted by sequence analysis of the putative E1 gene of isolates collected worldwide," *Proc. Natl. Acad. Sci.*, (1993) 90:8234–8238.

Farci, P. et al., "Lack of Protective Immunity Against Reinfection with Hepatitis C Virus," *Science* (1992) 258:135–140.

Prince, et al., "Immunity in Hepatitis C Infection," *J. Infect. Dis.*, (1992) 165:438–443.

Letvin, N.L., et al., "Vaccines Against Human Immunodeficiency Virus—Progress and Prospects," *N. Engl. J. Med.*, (1993) 329:1400.

Zibert, A., et al., "Antibodies in Human Sera Specific to Hypervariable Region 1 of Hepatitis C Virus Can Block Viral Attachment," *Virology*, (1995) 208:653–661.

Bukh, J., et al., "Genetic Heterogeneity of Hepatitis C Virus: Quasispecies and Genotypes," *Seminar in Liver Disease* (1995) 15:1, 41–63.

Farci, P., et al., "Prevention of hepatitis C virus infection in chimpanzees after antibody–mediated in vitro neutralization," *Proc. Natl. Acad. Sci.*, (1994) 91:7792–7796.

Shimuzu, Y. K., et al., "Neutralizing Antibodies against Hepatitis C Virus and the Emergence of Neutralization Escape Mutant Viruses," *J. Virol.*, (1994) 68:1494–1500.

Chayama, K. et al., Nucleotide sequence of hepatatis C virus (type 3b) isolated from a Japanese patient with chronic hepatitis C, *Journal of General Virology*, (1994) 75:3623–3628.

*Primary Examiner*—Laurie Scheiner
*Attorney, Agent, or Firm*—Morgan & Finnegan L.L.P.

[57] ABSTRACT

The nucleotide and deduced amino acid sequences of hypervariable region 1 of the envelope 2 gene of 49 isolates of hepatitis C are disclosed. The invention relates to the use of these sequences to design proteins and nucleic acid sequences useful in diagnostic methods and vaccines.

16 Claims, 24 Drawing Sheets

Alignment of HVR (nt) of HCV isolates of subtype 1a (I).

| SEQ ID NO | Isolate | | |
|---|---|---|---|
| 1 | S18 | 1 | GACACCTACgcCACtGGGGgAgTGCCaGcaGgACCacGcaGgCgtTCActAggtTCtTCt |
| 2 | S14 | 1 | GACACCTACaTCACCGGGGAACTGCCGGtCGCACCGtGggGaCacTCAgcAaTCTCcTCG |
| 3 | DK7 | 1 | agCACCcACGTCACCGGGGAACTGCCGcCCGCGCtGCGTtTGGcaTTACTAGTCTCTTtG |
| 4 | US11 | 1 | GAAACCTACGTCACCGGGGAAgTGCCGGCCAtGCCGCGTCTGGAcTTgCTgGTCTTTTCt |
| 5 | SW1 | 1 | GAAACCTACacCACCGGGGGGcTGCTGGtCAGACCGCGTCTGGAtTCaCCAGTCTTTTCA |
| 6 | DK9 | 1 | GACACCCgCGTCACCGGGGGAGCGCTGCcaGGAaCaCGTATGGACTCGCCAGTCTTcTCA |
| 7 | DR4 | 1 | GgCACCCAaGTCAgCGGGGGAGCGCcGCTCGCACCGtGaATGCACTCGCTGGTCTCTTCg |
| 8 | DR1 | 1 | acCACCCAtGTCActGGGGaAGtGaaGCTCGCgCCGcGtcTGCACTCaCTGGTCTCTTCa |
| 1-8 | consensus | | gacACC-acgtCAccGGGGG-agtGccg--cgcaccgcGt-tg-acTcactagtcTctTc- |

| SEQ ID NO | Isolate | | |
|---|---|---|---|
| 1 | S18 | 62 | CtCCGGGCGCCAAGCAGgACATCCAGCTaATcAAC |
| 2 | S14 | 62 | CACCGGGCGCCAAGCAGAACATCCAGCTGATtAAC |
| 3 | DK7 | 62 | CACCAGGCGCCAAaCAGAACATCCAaCTGATCAgC |
| 4 | US11 | 62 | CACaAGGCGCCCAGCAGAACATCCAGCTGATCAAC |
| 5 | SW1 | 62 | CgCgGGGCGCCCAGCAGAATATCCAGCTGgTCAAC |
| 6 | DK9 | 62 | gCCcGGGCGCCaAGCAGAATATtCAGCTGATCAAC |
| 7 | DR4 | 62 | aCCaGGGCGCGCGGCAGAATATCCAGTTGATCAAC |
| 8 | DR1 | 62 | cgCgGGGCGCGCGGCAGAAcgTCCAGTTGATCAAC |
| 1-8 | consensus | | caCcgGGCGCc-agCAGaAcaTcCAgcTgaTcAaC |

FIG. 1A

Alignment of HVR (nt) of HCV isolates of subtype 1b (II).

| SEQ ID NO | Isolate | | |
|---|---|---|---|
| 9 | D3 | 1 | cGTGgAggCgtGGGCACCCaCACGATAGGGGGGgCGCAAGCCtAcagCgtTAGggGgtTCa |
| 10 | D1 | 1 | aGTGcAtcCccGGGCACCCgCACGATAGGGGGGTCGCAAGCCaAacaCACTAGCAGtaTCg |
| 11 | P10 | 1 | cGCACCCaCACGACgGGGGGGTCGGtgGCCtACggCACCcGCAGGtTta |
| 12 | T10 | 1 | aGCACCCgCGTaACAGGGGGaACGGCAGCCCgCAaCACCtaCGGGCTCg |
| 13 | HK5 | 1 | GcCACCCACGTGACAGGGGGTACtGCAGCCCaCAcCACTcgtGGGCTCA |
| 14 | HK8 | 1 | GatACCtACGTGTCAGGGGGTGCGaCAGCCCGCAaCACTtACGGGCTtA |
| 15 | T3 | 1 | AcaACCcACGTGTCAGGGGGgGtGtCgGCtCGCAcCACCCACGGGCTgG |
| 16 | SW2 | 1 | AacACCTACACGACAGGGGGaGaGgCAGCCtaCAatACCCgCGGCTTtG |
| 17 | SA10 | 1 | GgGACCTACACGACAGGGGGGGCGCAAGgCcgCACCACCtcCAGCTTCG |
| 18 | US6 | 1 | GAGACtcACgtGACgGGGGGGCGCAAGCCtACgCCgCCcGCAGtTTCa |
| 19 | IND5 | 1 | CAGgCCAAgAcAATAGGGGGGcGcCAAGCCcACACCACCgGgcGCcTTg |
| 20 | IND8 | 1 | CACACCAACAtAATAGGGGGGAGgGAAGCCtcCACCACCCAagGCTTTA |
| 21 | HK3 | 1 | aGCACCcACAcGATAGGGGCaActGtgGCCCGCACCACtCAgaGtTggA |
| 22 | S9 | 1 | gGCACCacCGTGACgGGaGCGGtGcaAGGCCGTTCCctCCAAGGGCTCA |
| 23 | HK4 | 1 | aaCACCTACGTGACaGGGGgGGCGGCAaGCCaTTCCACCCgAGGGCTCA |
| 24 | S45 | 1 | ggtACCTACacGtCGGGGcaGGCGGCGGGCCGCACCACCgccGGGTTtA |
| 25 | DK1 | 1 | accACCcACgtGaCGGGGgcGGtGcaGGGCCGCACCACCcaaGGtTTcg |
| 9-25 | consensus | | -gtg-a--c--gggcaCccacatgacaGGgggggcggaagccc-caccacccgcgGgttca |

FIG. 1B-1

Alignment of HVR (nt) of HCV isolates of subtype 1b (II).

| SEQ ID NO | Isolate | | |
|---|---|---|---|
| 9 | D3 | 62 | cGTCCATaTTtTCAacTGGCCGgCTCAGAAgATCCAGCTTGTAAAC |
| 10 | D1 | 62 | tGTCCATgTTcTCActTGGCCGTCTCAGAAAATCCAGCTTGTAAAC |
| 11 | P10 | 50 | CGTCCcTCTTTaCAtCTGGGGCGTCTCAGAAAATCCAGCTTGTgAAC |
| 12 | T10 | 50 | CGTCCaTCTTTGCACCTGGGGCGTCTCAGAAgATCCAGCTTATAAAC |
| 13 | HK5 | 50 | CGTCCCTgTTCGCCCCTGGGcCTTCTCAGAAAATCCAGCTTATAAAt |
| 14 | HK8 | 50 | CGTCCCTCTTCaCCCCaGGGgCTgCTCAGAAAATCCAGCTTATAAAC |
| 15 | T3 | 50 | CaTCCtTCTTtTCACCtGGGCCGTCTCAGAAAATCCAGCTCGTAAAC |
| 16 | SW2 | 50 | CGaGTaTCTTCTCAagcGGGCCGTCTCAGAAAATCCAGCTCGTAAAC |
| 17 | SA10 | 50 | tGgGTCTCTTCACcCCTGGGCCGTCTCAGAgAATCCAGCTCGTAAAC |
| 18 | US6 | 50 | cGTCTCTCTTCACaCCTGGGtCacgTCAGAAtATCCAGCTTaTAAAC |
| 19 | IND5 | 50 | tGTCTaTgTTCACCCCTGGGcCGTCCCAGAAcATCCAGCTTGTAAAC |
| 20 | IND8 | 50 | CGaGTcTtTTCAGCCCTGGagCGTCCCAGAAAATCCAGCTTGTAAAC |
| 21 | HK3 | 50 | CGGGCtTcTTCAGCTCcGGgCCcTCTCAGAAAATCCAGCTTaTAAAT |
| 22 | S9 | 50 | CtGGCCTTTTttCCTCtGGaCCGaCTCAGAAAcTCCAGCTTgTAAAT |
| 23 | HK4 | 50 | CGTCCCTTTTcACaaCgGGGgCGtCTCAGAAAATCCAGCTTATAAAC |
| 24 | S45 | 50 | CGTCCaTCTTtAacCCtGGGTCGGCTCAGAgcATCCAGCTcATAAAC |
| 25 | DK1 | 50 | CGTCCcTCTTctcaCCcGGaTCGGCcCAGAaaATCCAGCTtgTAAAC |
| 9-25 | consensus | | cgtcccTcTTcacacctGGgcCgtctCAGAaaaTCCAGCTtgTaAAc |

FIG. 1B-2

Alignment of HVR (nt) of HCV isolates of genotype 1.

| SEQ ID NO | Isolate | | |
|---|---|---|---|
| 9 | D3 | 1 | cGTGgAggCgtGGGCACCCaCACGATAGGGGGGgCGCAAGCCtAcagCgtTAGggGgtTCa |
| 10 | D1 | 1 | aGTGcAtcCccGGGCACCCgCACGATAGGGGGGTCGCAAGCCaAacaCACTAGCAGtaTCg |
| 11 | P10 | 1 | cGCACCCaCACGACgGGGGGGTCGGtgGCCtACggCACCcGCAGGtTta |
| 12 | T10 | 1 | aGCACCCgCGTaACAGGGGGaACGGCAGCCCgCAaCACCtaCGGGCTCg |
| 13 | HK5 | 1 | GcCACCCACGTGACAGGGGGTACtGCAGCCCaCAcCACTcgtGGGCTCA |
| 14 | HK8 | 1 | GatACCtACGTGTCAGGGGGTGCGaCAGCCCGCAaCACTtACGGGCTtA |
| 15 | T3 | 1 | AcaACCcACGTGTCAGGGGGgGtGtCgGCtCGCAcCACCCACGGGCTgG |
| 16 | SW2 | 1 | AacACCTACACGACAGGGGGaGaGgCAGCCtaCAatACCCgCGGCTTtG |
| 17 | SA10 | 1 | GgGACCTACACGACAGGGGGGGCGCAAGgCcgCACCACCtcCAGCTTCG |
| 18 | US6 | 1 | GAGACtcACgtGACgGGGGGGGCGCAAGCCtACgCCgCCcGCAGtTTCa |
| 19 | IND5 | 1 | CAGgCCAAgAcAATAGGGGGGcGcCAAGCCcACACCACCgGgcGCcTTg |
| 20 | IND8 | 1 | CACACCAACAtAATAGGGGGGAGgGAAGCCtcCACCACCCAagGCTTTA |
| 21 | HK3 | 1 | aGCACCcACAcGATAGGGGCaActGtgGCCCGCACCACtCAgaGtTggA |
| 22 | S9 | 1 | gGCACCacCGTGACgGGaGCGGtGcaAGGCCGTTCCctCCAAGGGCTCA |
| 23 | HK4 | 1 | aACACCTACGTGACaGGGGGGGCGGCAaGCCATTCCaCCCgAGGGCTCA |
| 5 | SW1 | 1 | GAaACCTACacCACCGGGGGGGCtGCtGGTCAgACCGCGtcTGGAtTCA |
| 7 | DR4 | 1 | GGCACCCAaGTCAgCGGGGGGAgcGCCGCTCGCACCGtGaaTGcAcTCg |
| 3 | DK7 | 1 | aGCACCCACGTCACCGGGGGaAcTGCCGCCCGCgCtGCGttTGgcaTtA |
| 1 | S18 | 1 | GaCACCTACGCCACtGGGGGAgTGCCaGCaGgACCACGcagGcGTTcA |
| 24 | S45 | 1 | GgtACCTACaCGtCGGGGcaGGcGGCGGGCCGCACCACCgccGGGTTtA |
| 25 | DK1 | 1 | accACCcACGTGACGGGGGcGGtGcaGGGCCGCACCACCcaaGGtTTcG |
| 4 | US11 | 1 | GAaACCTACGTCACCGGGGGAAgTGCCGGCCatgCCGCGtctGGACTtG |
| 2 | S14 | 1 | GACACCTACaTCACCGGGGGAAcTGCCGGtCGcACCGtGgggacACTCa |
| 6 | DK9 | 1 | GACACCCgCGTCACCGGGGGgAGcGCtGCCaGgAaCaCGTaTGgACTCg |
| 8 | DR1 | 1 | acCACCCatGTCACtGGGGGaAGtGaaGCtcGcgcCgCGTcTGcACTCa |
| 1-25 | consensus | | -gtg-a--c--ggacaCccacgtgacaGGgggg-cggcagcccgcaccacccacgggctca |

FIG. 1C-1

Alignment of HVR (nt) of HCV isolates of genotype 1.

| SEQ ID NO | Isolate | | |
|---|---|---|---|
| 9 | D3 | 62 | cGTCCATaTTtTCAacTGGCCGgCTCAGAAgATCCAGCTTGTAAAC |
| 10 | D1 | 62 | tGTCCATgTTcTCActTGGCCGTCTCAGAAAATCCAGCTTGTAAAC |
| 11 | P10 | 50 | CGTCCcTCTTTaCAtCTGGGGCGTCTCAGAAAATCCAGCTTGTgAAC |
| 12 | T10 | 50 | CGTCCaTCTTTGCACCTGGGGCGTCTCAGAAgATCCAGCTTATAAAC |
| 13 | HK5 | 50 | CGTCCCTgTTCGCCCCTGGGcCTTCTCAGAAAATCCAGCTTATAAAt |
| 14 | HK8 | 50 | CGTCCCTCTTCaCCCCaGGGgCTgCTCAGAAAATCCAGCTTATAAAC |
| 15 | T3 | 50 | CaTCCtTCTTtTCACCtGGGCCGTCTCAGAAAATCCAGCTCGTAAAC |
| 16 | SW2 | 50 | CGaGTaTCTTCTCAagcGGGCCGTCTCAGAAAATCCAGCTCGTAAAC |
| 17 | SA10 | 50 | tGgGTCTCTTCACcCCTGGGCCGTCTCAGAgAATCCAGCTCGTAAAC |
| 18 | US6 | 50 | cGTCTCTCTTCACaCCTGGGtCacgTCAGAAtATCCAGCTTaTAAAC |
| 19 | IND5 | 50 | tGTCTaTgTTCACCCCTGGGcCGTCCCAGAAcATCCAGCTTGTAAAC |
| 20 | IND8 | 50 | CGaGTcTtTTCAGCCCTGGagCGTCCCAGAAAATCCAGCTTGTAAAC |
| 21 | HK3 | 50 | CGGGCtTcTTCAGCTCcGGgCCcTCTCAGAAAATCCAGCTTaTAAAT |
| 22 | S9 | 50 | CtGGCCTTTTttCCTCtGGaCCGaCTCAGAAAcTCCAGCTTgTAAAT |
| 23 | HK4 | 50 | CgtcCCTTTTCACaaCGGGgGCGtCTCAGAAAATCCAGCTTaTAAAC |
| 5 | SW1 | 50 | CcaGTCTTTTCACgCgGGGCGCcCaGCAGAATATCCAGCTGgTCAAC |
| 7 | DR4 | 50 | CTgGTCTCTTCGacCaGGGCGCgCgGCAGAATATCCAGtTGATCAAC |

FIG. 1C–2

| | | | |
|---|---|---|---|
| 3 | DK7 | 50 | CTAGTCTCTTtGCaCCaGGCGCCAAaCAGAACATCCAaCTGATCAgC |
| 1 | S18 | 50 | CTAGgtTCTTctCtCCgGGCGCCAAgCAGgACATCCAGCTaATCAAC |
| 24 | S45 | 50 | CGTCCaTCTTtaacCCtGGgTCGGCtCAGAgCATCCAGCTcATAAAC |
| 25 | DK1 | 50 | CGTCCCTCTTCTCACCcGGaTCGGCcCAGAAaATCCAGCTtgTAAAC |
| 4 | US11 | 50 | CtggTCTtTTCTCACaaGGCGCCcAGCAGAACATCCAGCTGATcAAC |
| 2 | S14 | 50 | gCAaTCTcCTCgCACCGGGCGCCAAGCAGAACATCCAGCTGATtAAC |
| 6 | DK9 | 50 | CCAGTCTTtCTCAgcCCGGGCGCCAAGCAGAAtATtCAGCTGATCAAC |
| 8 | DR1 | 50 | CtgGTCTctTCAcgCgGGGCGCgcgGCAGAAcgTcCAGtTGATCAAC |
| 1-25 | consensus | | cgt--cTctTcacacctGGggCgtctCAGaaaaTcCAgcTtaTaAac |

FIG. 1C-3

Alignment of HVR (nt) of HCV isolates of subtype 2a (III).

| SEQ ID NO | Isolate | | |
|---|---|---|---|
| 26 | US10 | 1 | gcaaCCAggACggTTGGGcaTtCTGcaGCGtaCACCgCCtccacttTCgCCGGCaTcTTCa |
| 27 | T4 | 1 | AgCtCCAccACcaTTGGGaGTgCTGtCGCGagCACCaCCagaGGCCTCACCGGCtTgTTCt |
| 28 | T9 | 1 | AcCACCcAtACatCTGGGgGcACcGCCGGGCaTACagCCtAtGGCCTCACCaGCaTCTTCA |
| 29 | T2 | 1 | caCACCgAgctcaCcGGGaGtAatGCCGGGCgTACcaCCcAgGGCCTCgCtgcCtTCTTCA |
| 26-29 | consensus | | accaCCaagacca-tGGGagtactGccG-Gc--ACc-CCta-ggccTC-CcggC-TcTTCa |

| SEQ ID NO | Isolate | | |
|---|---|---|---|
| 26 | US10 | 62 | aCgCtGGCTCTagGCAGAACATCCAGCTCATcAAC |
| 27 | T4 | 62 | cCCCaGGCTCTCaGCAGAACATCCAGCTCATTAAC |
| 28 | T9 | 62 | gCCCTGGCGCcCGGCAGAAaATCCAGCTCATTtAt |
| 29 | T2 | 62 | cCCCTGGCGCtaGcCAGAgggTtCAGCTCATTaAc |
| 26-29 | consensus | | cCcCtGGC-Ct-ggCAGAacaTcCAGCTCATtaAc |

FIG. 1D

Alignment of HVR (nt) of HCV isolates of subtype 2b (IV).

| SEQ ID NO | Isolate | | |
|---|---|---|---|
| 30 | T8 | 1 | aCCACcTATACtACCGGCGcACAAGtGGCTcGtacCACtgctaGtCTTGCcgGCCTCTTCa |
| 31 | DK8 | 1 | gCCACtTATACCACCGGCGgACAAGCGGCTaGGgaCACCtgggGGCTTGCTcGCCTCTTCt |
| 32 | DK11 | 1 | aaCACccgTgtCACCGGCGcgatcGCGGgTcGGacCgCCgcatcGCTTGCTaGCCTCTTta |
| 30-32 | consensus | | acCACctaTaccACCGGCGcacaaGcGGcTcGgacCaCcgc--ggCTTGCt-GCCTCTTca |

| SEQ ID NO | Isolate | | |
|---|---|---|---|
| 30 | T8 | 62 | CCaCcGGtcCtCAGCAGAAAaTCAacTTaATCAAt |
| 31 | DK8 | 62 | CCcCTGGCgCCCAGCAGAAAcTCAgTTTGATCAAC |
| 32 | DK11 | 62 | aCtCTGGCcCCCAGCAGAAAaTCAaTTTGATCAAC |
| 30-32 | consensus | | cC-CtGGccCcCAGCAGAAAaTCAatTTgATCAAc |

FIG. 1E

Alignment of HVR (nt) of HCV isolates of genotype 2.

| SEQ ID NO | Isolate | | |
|---|---|---|---|
| 30 | T8 | 1 | aCCACcTATACtACCGGCGcACAAGtGGCTcGtacCACtgctaGtCTTGCcgGCCTCTTCa |
| 31 | DK8 | 1 | gCCACtTATACCACCGGCGgACAAGCGGCTaGGgaCACCtgggGGCTTGCTcGCCTCTTCt |
| 32 | DK11 | 1 | AaCACCCgTgtCACCGGCGcgAtCGCGGGTCGGACCGCCgcatcGCTTGCTAGCCTCTTtA |
| 28 | T9 | 1 | AcCACCCaTACatCTGGGGGcACCGCCGGGCatACaGCCtatGGCCTCACCAGCaTCTTCA |
| 27 | T4 | 1 | AgCtCCAccACcaTTGGGaGTgCTGtCGCGagCACCaCCagaGGCCTCACCGGCtTgTTCt |
| 26 | US10 | 1 | gcaACCAgGACggTTGGGcaTtCTGCaGCGtaCACCgCCtccacttTCGCCGGCaTCTTCA |
| 29 | T2 | 1 | caCACCgAGctCACcGGGagTaaTGCcGGGCgtACCaCCCAGgGCcTCGCtGcCtTCTTCA |
| 33 | S83 | 1 | acCACttAtacCACtGGagcatcTGCtGGaCagcaggtaCAGaGCtTCGCcagacTCTTCA |
| 26-33 | consensus | | accaCctataccac-GGggg-actGc-G-gcg-acc-cct-gggccTcgCcggccTcTTca |

| SEQ ID NO | Isolate | | |
|---|---|---|---|
| 30 | T8 | 62 | CCaCcGGtcCtCAGCAGAAAaTCAacTTaATCAAt |
| 31 | DK8 | 62 | CCcCTGGCgCCCAGCAGAAAcTCAgTTTGATCAAC |
| 32 | DK11 | 62 | aCtCTGGCcCCCAGCAGAAAATCAATTTGATCAAC |
| 28 | T9 | 62 | gCCCTGGCgCCCgGCAGAAAATCCAGCTCATTtAt |
| 27 | T4 | 62 | cCCCaGGCTCTCaGCAGAACATCCAGCTCATTAAC |
| 26 | US10 | 62 | aCgCTGGCTCTAGGCAGAACATCCAGCTCATcAAC |
| 29 | T2 | 62 | cCCCTGGCgCTAGCCAGAggGTtCAGCTCATtAAC |
| 33 | S83 | 62 | gtCCgGGgcCcAaCCAGcatGTcCAGCTCgTccgC |
| 26-33 | consensus | | cccCtGGc-C-cagCAGaaaaTccagcTcaTcaac |

FIG. 1F

Alignment of HVR (nt) of HCV isolates of subtype 3a (V).

| SEQ ID NO | Isolate | | |
|---|---|---|---|
| 34 | HK10 | 1 | GggACATATaTCAgtGGTGGCcacGtgGCTCGTgGTGCctcggGGCTcGCcAGCTTtTTTT |
| 35 | S2 | 1 | GAAACATATGTCACCGGTGGCAGTGcAGCTCGTAGTGCTAGtaGGCTAGCTAGCTTcTTTT |
| 36 | S52 | 1 | GAAACATATGTCACCGGTGGCAGTGtAGCTCATAGTGCTAGAGGGtTAACTAGCCTTTTTA |
| 37 | S54 | 1 | GCAACATATacCACCGGTGGCAGTGCAGCTCATAGTGCCCaAGGGaTAACTcGCCTTTTTA |
| 38 | DK12 | 1 | aCcACAcAcgtCACCGGTGGCgaTGCAGCTCgTAGTaCCCtcaGGtTtACTaGCCTTTTTA |
| 34-38 | consensus | | g-aACAtAtgtCAccGGTGGCagtGcaGCTCgTaGTgCc-gagGG-TaaCtaGCcTtTTTa |

| SEQ ID NO | Isolate | | |
|---|---|---|---|
| 34 | HK10 | 62 | CTCCGGGCGCCaAaCAGAAcCTGCAGCTGaTcAAt |
| 35 | S2 | 62 | CTCCGGGCGCCcAGCAGAAACTGCAGCTGGTtAAC |
| 36 | S52 | 62 | GTaTGGGCGCCAAGCAGAAACTGCAGTTGGTCAAC |
| 37 | S54 | 62 | GTGTGGGCGCCAAaCAGAAcCTGCAGTTGGTCAAC |
| 38 | DK12 | 62 | GTGTGGGCtCCAAcCAGcAaCTGCAGcTaGTCAAC |
| 34-38 | consensus | | gT-tGGGCgCCaA-CAGaAaCTGCAGcTggTcAAc |

FIG. 1G

Alignment of HVR (nt) of HCV isolates of subtype 4c.

| SEQ ID NO | Isolate | | |
|---|---|---|---|
| 41 | Z7 | 1 | acGACCaTGACAACcGGGGGAgctGcTGCcCGCActgCCCacGCCtTcACCgGCCTtTTCA |
| 42 | Z6 | 1 | gaGACCgTGACAACtGGGGGAagcGtTGCtCGCAgcaCCCggGCCaTtACtaGCCTcTTCA |
| 41-42 | consensus | | --GACC-TGACAAC-GGGGGA---G-TGC-CGCA---CCC--GCC-T-AC--GCCT-TTCA |

| SEQ ID NO | Isolate | | |
|---|---|---|---|
| 41 | Z7 | 62 | cTTCTGGGCCccAGCAaAAatTACAGCTCATTAAc |
| 42 | Z6 | 62 | aTTCTGGGCCtaAGCAgAAccTACAGCTCATTAAt |
| 41-42 | consensus | | -TTCTGGGCC--AGCA-AA--TACAGCTCATTAA- |

FIG. 1H

Alignment of HVR (nt) of HCV isolates of genotype 4.

| SEQ ID NO | Isolate | | |
|---|---|---|---|
| 43 | DK13 | 1 | ggCACcTACGtcaCcGGgGgccaGGCgGGaCagACCgCgTtTcaCcTTaCCGGaCTgTTcA |
| 40 | Z1 | 1 | acCACgTACGcttCtGGcGctgCGGCcGGCCGAACCaCCTcTGGCTTTgCCGGCCTaTTTA |
| 39 | Z4 | 1 | caCACaTctGtcAgCGGGGGcaCTcagGCCCGAgCaGCCCAaGGgTTgACCaGCCTcTTTA |
| 41 | Z7 | 1 | acGACCaTGACAACCGGGGGAgCTGcTGCCCGCACtGCCCAcGCCTTcACCgGCCTtTTCA |
| 42 | Z6 | 1 | gaGACCgTGACAACtGGGGGAagcGtTGCtCGCAgcaCCCggGCCaTtACtaGCCTcTTCA |
| 39-43 | consensus | | --cACct--gc-accGGgGg--c-gc-GccCg-accgCccatg-ctTtaCcgGcCTcTTcA |

| SEQ ID NO | Isolate | | |
|---|---|---|---|
| 43 | DK13 | 62 | CCaggGGttCCcAcCAGAACATaCaGCTcATtAAC |
| 40 | Z1 | 62 | CCcCTGGcgCCAAgCAGAACATCCgGCTtATcAAC |
| 39 | Z4 | 62 | CaTCTGGGCCCAgaCAAAACcTCCAGCTgATaAAt |
| 41 | Z7 | 62 | CTTCTGGGCCCcAGCAAAAatTACAGCTCATTAAc |
| 42 | Z6 | 62 | aTTCTGGGCCtaAGCAgAAccTACAGCTCATTAAt |
| 39-43 | consensus | | c-tctGGgcCcaagCAgAAc-TaCaGCTcATtAAc |

FIG. 1I

Alignment of HVR (nt) of HCV isolates of subtype 5a.

| SEQ ID NO | Isolate | | |
|---|---|---|---|
| 44 | SA6 | 1 | aGCACCCACAgtGTGGggGGctCtGCaGCTcAtAcTACGaGcGGCTTTaCCTCacTTTTCA |
| 45 | SA1 | 1 | cGCACCCACACcGTGGccGGTACcGCtGCTtAcAGTACGCGaGGCTTTGCCTCgaTTTTCA |
| 46 | SA13 | 1 | AACACCCgCACTGTGGGtGGTAgTGCgGCccAAgGcGCGCGcGGgcTcGCTTCACTTTTCA |
| 47 | SA4 | 1 | AACACCCACATTtcGGGCGGTACTGCTGCTaAAAcTGtGCaaGGttTtaCTTCACTTTTCt |
| 48 | SA7 | 1 | AACACtCACgTTgtGGGCGGTgCcGCTGCTcgtAgTGcGagtGGcaTggCcTCACTcTTta |
| 44-48 | consensus | | aaCACcCaCa-tgtGGgcGGtactGCtGCtca-agtgcGcg-GGctTtgCcTCacTtTTca |

| SEQ ID NO | Isolate | | |
|---|---|---|---|
| 44 | SA6 | 62 | aCCCCGGGCCgAAGCAGAACTTGCAGCTCATAtAc |
| 45 | SA1 | 62 | CCCCCGGGCCaAAGCAGAACTTGCAGCTCATAAAT |
| 46 | SA13 | 62 | CCCCtGGGCCgCAGCAGAACTTGCAGCTCATAAAT |
| 47 | SA4 | 62 | CCtTCGGGGCACAGCAGAATTTGCAGCTCATAAAT |
| 48 | SA7 | 62 | CtgTCGGGGCAaAGCAGAATTTGCAGCTCATAAAT |
| 44-48 | consensus | | cccccGGGcCaaAGCAGAAcTTGCAGCTCATAaAt |

FIG. 1J

Alignment of HVR (nt) of 49 HCV isolates of genotypes 1-6.

| SEQ ID NO | Isolate | | |
|---|---|---|---|
| 49 | HK2 | 1 | ACcaccACCACcGGccacgCaGtgGGcCgcacaacctccAGCcTtG |
| 33 | S83 | 1 | aCcACttatACCACTGGagcaTCTGCtGGaCAgcagGtacagAGCTTCG |
| 26 | US10 | 1 | gCaACCAgGACggTTGGGcatTCTGCAGCgtACACCGCCtccActTTCG |
| 19 | IND5 | 1 | CAggCCAAGACAATAGGGGGGcGccAAGCCcACACCACCgggcGCcTTG |
| 20 | IND8 | 1 | CACACCAACAtAATAGGGGGGaGGGAAGCCTcCACCACCCaaGGCTTTa |
| 16 | SW2 | 1 | aACACCtACACGACAGGGGGagaGGcAGCCTACAatACCCGCGGCTTTg |
| 11 | P10 | 1 | cGCACCcACACGACGGGGGGGtCGGtGGCCTACggCACCCGCaGGTTTA |
| 24 | S45 | 1 | GGtACCTACACGtCGGGGcaGGCGGcGGGCCGCACCACCgCCgGGTTTA |
| 17 | SA10 | 1 | GGGACCTACACGACaGGGGGGGCGCAAGGCCGCACCACCtCCAGcTTCg |
| 18 | US6 | 1 | GaGACtCACGTGACGGGGGGGGCGCAAGcCtaCgCCgCCCgCAGTTTCa |
| 25 | DK1 | 1 | ACcACCCACGTGACGGGGGcGGTGCAGGgCCGCACCACCCAaGGTTTCG |
| 15 | T3 | 1 | ACaACCCACGTGtCAGGGGGGGTGtCGGCtCGCACCACCCACGGGCTgG |
| 12 | T10 | 1 | AgcACCCgCGTaaCAGGGGGaaCGgCAGCCCGCAACACCTACGGGCTcG |
| 14 | HK8 | 1 | gAtACCTACGTGtCAGGGGGtGCGaCAGCCCGCAACACtTACGGGCTtA |
| 23 | HK4 | 1 | aACACCTACGTGACAGGGGGgGCGGCAagCCAttCCACcCGaGGGCTCA |
| 13 | HK5 | 1 | gcCACCcACGTGACAGGGGGTACTGCAGcCCAcACCACtCGtGGGCTCA |
| 29 | T2 | 1 | caCACCgAgcTCACcGGGAGTAaTGCCGgGCGtACCACCCagGGCCTCg |
| 27 | T4 | 1 | AgCtCCaccACCAtTGGGAGTgCTGtCGcGaGcACCACCagaGGCCTCA |
| 28 | T9 | 1 | ACCACCcAtACaTCTGGGGGcaCcGCCGGGCatACagCCTaTGGCCTCA |
| 40 | Z1 | 1 | ACCACgTAcgCTTCTGGCGCtgCgGCCGGcCGaACCACCTCTGGCtTTG |
| 30 | T8 | 1 | ACCACCTATaCTACCGGCGCacaaGtGGcTCGtACCACtGCTaGtCTTG |
| 32 | DK11 | 1 | AaCACCcgTgtCACCGGCGCgatcGCGGgTCGGACCgCCGCatcGCTTG |
| 31 | DK8 | 1 | GcCACtTATAcCACCGGCGGaCAaGCGGCTaGGGaCaCCTgGGGGCTTG |

FIG. 1K-1

Alignment of HVR (nt) of 49 HCV isolates of genotypes 1-6.

| | | | |
|---|---|---|---|
| 34 | HK10 | 1 | GggACATATATCAgtGGTGGCCAcGtGGCTCGTGGTGCCTcGGGGCTcG |
| 35 | S2 | 1 | GAAACATATGTCACCGGTGGCAGTGcAGCTCGTAGTGCTAGtaGGCTAG |
| 36 | S52 | 1 | GAAACATATGTCACCGGTGGCAGTGtAGCTCATAGTGCTAGAGGGtTAA |
| 37 | S54 | 1 | GCAACATATacCACCGGTGGCAGTGCAGCTCATAGTGCCCaAGGGaTAA |
| 38 | DK12 | 1 | ACCACACACGTCACCGGTGGCgaTGCAGCTCGTAGTaCCCTcaGGtTTA |
| 3 | DK7 | 1 | AgCACCCACGTCACCGGGGGAAcTGCCGCCCGcGCTGCGTTTGGcaTTA |
| 4 | US11 | 1 | GAAACCTACGTCACCGGGGGAAgTGCCGGCCAtGCCGCGTCTGGAcTTg |
| 5 | SW1 | 1 | GAAACCTACacCACCGGGGGGgcTGCTGGtCAGACCGCGTCTGGAtTCa |
| 6 | DK9 | 1 | GACACCcgCGtCACCGGGGGGAGcGCTGcCAGGAaCACGTATGGAcTCg |
| 1 | S18 | 1 | GACACCTACGcCACtGGGGGGAGTGCCaGCAGGACCACGcAGGCgtTCA |
| 2 | S14 | 1 | GACACCTACaTCACcGGGGGAAcTGCCGGTCGCACCGtGggGaCACTCA |
| 8 | DR1 | 1 | acCACCCAtGTCACtGGGGGAAGTGaaGCTCGCgCCGcGtcTGCACTCA |
| 7 | DR4 | 1 | GGCACCCAaGTCAgCGGGGGgAGcGCcGCTCGCACCGtGaaTGCACTCg |
| 43 | DK13 | 1 | GGCACCtACGTCAcCGGGGGCcagGCgGgaCAgACCGCGttTcaCCTTA |
| 44 | SA6 | 1 | aGCACCCACAgtGTGGGGGGCtCtGCaGCTCAtACTACGaGcGGCTTTA |
| 45 | SA1 | 1 | cGCACCCACACcGTGGccGGTACcGCtGCTtAcAGTACGCGaGGCTTTG |
| 46 | SA13 | 1 | aACACCCgCACtGTGGGtGGTAGtGCgGCcCAagGCgCGCGcGGgcTcG |
| 42 | Z6 | 1 | gAGACCgTGACAACtGGGGGAAGcGtTGCtCGCAGCaCCCGgGCCaTtA |
| 41 | Z7 | 1 | AcGACCaTGACAACcGGGGGAgCTGcTGCCCGCACtgCCCAcGCCTTcA |
| 21 | HK3 | 1 | AGCACCcaCACGAtaGGGGCAaCTGtgGCCCGCACCaCtCAgaGtTggA |
| 22 | S9 | 1 | gGCACCaCCGTGAcgGGaGCggtgCAaGgCCGttCCctCCAAGGGcTcA |
| 39 | Z4 | 1 | cACACatCtGTcAgcGGgGGcaCtCAgGCCCGagCaGCCCAAGGGtTGA |
| 48 | SA7 | 1 | AACACtCACGTTgtGGGCGGTgCcGCTGCTCGtAgTGCGagtGGcaTGg |
| 47 | SA4 | 1 | AACACCCACATTtcGGGCGGTaCtGCTGCTaAaAcTGTGcaaGGtTTtA |
| 9 | D3 | 1 | cGTGgAggCgtGGGCACCCACACGATAGGGGGGgCGCAAGCCtAcAgCGTTAGgGGgTTCA |
| 10 | D1 | 1 | aGTGcAtcCccGGGCACCCgCACGATAGGGGGGtCGCAAGCCaAacaCacTAGcaGtaTCg |
| 1-49 | consensus | | -gtg-a--c--ggacaCccacatcaccGgggggactgcagcccgcaccacccgcgggctca |

FIG. 1K-2

Alignment of HVR (nt) of 49 HCV isolates of genotypes 1-6.

| SEQ ID NO | Isolate | | |
|---|---|---|---|
| 49 | HK2 | 47 | CCgGgCTtTTCtccCCcGGtgCCAAgCAaaATcTaCAaCTtaTCaaC |
| 33 | S83 | 50 | CCaGaCTCTTCAgtCCgGGgcCCAAcCAGcATgTCCAGCTCgTCcgC |
| 26 | US10 | 50 | CCgGcATCTTCAaCgCTGGctCtAggCAGAACATCCAGCTCaTCAAC |
| 19 | IND5 | 50 | tGtcTATgTTCAcCCCTGGgcCGTCCCAGAACATCCAGCTTGTAAAC |
| 20 | IND8 | 50 | CGAGTcTtTTCAgCCCTGGagCGTCCCAGAAAATCCAGCTTGTAAAC |
| 16 | SW2 | 50 | CGAGTaTCTTCtCAagcGGGcCGTCTCAGAAAATCCAGCTcGTAAAC |
| 11 | P10 | 50 | CGTCCcTCTTTACAtCTGGGgCGTCTCAGAAAATCCAGCTtGTgAAC |
| 24 | S45 | 50 | CGTCCaTCTTTAaCCCTGGGtCGgCTCAGAGcATCCAGCTCaTAAAC |
| 17 | SA10 | 50 | tGggTCTCTTCACCCCTGGGcCGtCTCAGAGaATCCAGCTCgTAAAC |
| 18 | US6 | 50 | CGTCTCTCTTCACACCTGGGTCacgTCAGAAtATCCAGCTTaTAAAC |
| 25 | DK1 | 50 | CGTCCCTCTTCTCACCcGGaTCGgCcCAGAAAATCCAGCTTGTAAAC |
| 15 | T3 | 50 | CaTCCtTCTTTTCACCTGGGcCGTCTCAGAAAATCCAGCTcGTAAAC |
| 12 | T10 | 50 | CGTCCaTCTTTgCACCTGGGGCGTCTCAGAAgATCCAGCTTATAAAC |
| 14 | HK8 | 50 | CGTCCCTCTTCACcCCaGGGGCtgCTCAGAAAATCCAGCTTATAAAC |
| 23 | HK4 | 50 | CGTCCCTtTTCACaaCgGGGGCgTCTCAGAAAATCCAGCTTATAAAC |
| 13 | HK5 | 50 | CGTCCCTgTTCgCCCCTGGGcCTTCTCAGAAAATCCAGCTTATAAAt |
| 29 | T2 | 50 | CtGCCTTcTTCaCCCCTGGCgCTagcCAGAgggTtCAGCTCATTAAC |
| 27 | T4 | 50 | CCGGCTTgTTCtCCCCaGGCtCTCaGCAGAAcATCCAGCTCATTAAC |
| 28 | T9 | 50 | CCaGCaTcTTCAgCCCTGGCGCCCgGCAGAAaATCCAGCTCATTtAt |
| 40 | Z1 | 50 | CCGGCCTaTTtACCCCTGGCGCCaAGCAGAAcATCCgGCTtATCAAc |
| 30 | T8 | 50 | CCGGCCTCTTcACCaCcGGtCCtCAGCAGAAAATCAAcTTaATCAAt |
| 32 | DK11 | 50 | CTaGCCTCTTtAaCtCTGGCCCCCAGCAGAAAATCAATTTGATCAAC |
| 31 | DK8 | 50 | CTcGCCTCTTcTCCCCTGGCGCCCAGCAGAAACTCAgTTTGATCAAC |
| 34 | HK10 | 50 | CcAGCTTtTTTTCTCCGGGCGCCaAaCAGAAcCTGCAGCTGATCAAt |
| 35 | S2 | 50 | CTAGCTTcTTTTCTCCGGGCGCCcAGCAGAAACTGCAGCTGGTtAAC |

FIG. 1K-3

Alignment of HVR (nt) of 49 HCV isolates of genotypes 1-6.

| SEQ ID NO | Isolate | | |
|---|---|---|---|
| 36 | S52 | 50 | CTAGCCTTTTTAGTaTGGGCGCCAAGCAGAAACTGCAGTTGGTCAAC |
| 37 | S54 | 50 | CTcGCCTTTTTAGTGTGGGCGCCAAaCAGAAcCTGCAGTTGGTCAAC |
| 38 | DK12 | 50 | CTAGCCTTTTTAGTGTGGGCtCCAAcCAGcAaCTGCAGCTaGTCAAC |
| 3 | DK7 | 50 | CTAGTCTcTTTgCACcAGGCGCCAAaCAGAACATCCAaCTGATCAgC |
| 4 | US11 | 50 | CTgGTCTTTTCtCACaAGGCGCCCAGCAGAACATCCAGCTGATCAAC |
| 5 | SW1 | 50 | CCAGTCTTTTCACgCgGGGCGCCCAGCAGAATATCCAGCTGgTCAAC |
| 6 | DK9 | 50 | CCAGTCTTcTCAgcCCGGGCGCCAAGCAGAATATtCAGCTGATCAAC |
| 1 | S18 | 50 | CtAGgtTCtTCtCtCCGGGCGCCAAGCAGgACATCCAGCTaATCAAC |
| 2 | S14 | 50 | gcAaTCTCcTCgCaCCGGGCGCCAAGCAGAACATCCAGCTGATtAAC |
| 8 | DR1 | 50 | CTGGTCTCTTCaCgCgGGGCGCGCGGCAGAACgTCCAGTTGATCAAC |
| 7 | DR4 | 50 | CTGGTCTCTTCgaCCaGGGCGCGCGGCAGAAtATCCAGTTGATCAAC |
| 43 | DK13 | 50 | CCGGACTgTTCAcCagGGGttCcCAcCAGAACATaCAGCTCATtAAC |
| 44 | SA6 | 50 | CCTCACTTTTCAaCCCCGGGCCgAAGCAGAACTTGCAGCTCATAtAC |
| 45 | SA1 | 50 | CCTCgaTTTTCACCCCCGGGCCaAAGCAGAACTTGCAGCTCATAAAT |
| 46 | SA13 | 50 | CTTCaCTTTTCACCCCTGGGCCgcAGCAGAACTTGCAGCTCATAAAT |
| 42 | Z6 | 50 | CTaGCCTcTTCAaTTCTGGGCCtaAGCAGAACcTACAGCTCATTAAT |
| 41 | Z7 | 50 | CcGGCCTtTTCAcTTCTGGGCCCcAGCAaAAAtTACAGCTCATTAAc |
| 21 | HK3 | 50 | CgGGCtTcTTCAgCTCcGGGCCCtCTCAGAAAaTCCAGCTTATAAAT |
| 22 | S9 | 50 | CtGGCCTtTTTtCCTCTGGaCCgACTCAGAAACTCCAGCTTgTAAAT |
| 39 | Z4 | 50 | CCaGCCTCTTTACaTCTGGGCCcAgaCAaAAcCTCCAGCTgATAAAT |
| 48 | SA7 | 50 | CCTCACTCTTTACtgTCGGGGCAAAGCAGAATTTGCAGCTCATAAAT |
| 47 | SA4 | 50 | CtTCACTtTTcTCctTCGGGGCAcAGCAGAATTTGCAGCTCATAAAT |
| 9 | D3 | 62 | CGTCCATaTTtTCAacTGGGCCGgCTCAGAAgATCCAGCTTGTAAAC |
| 10 | D1 | 62 | tGTCCATgTTcTCActTGGGCCGtCTCAGAAaATCCAGCTTGTAAAC |
| 1-49 | consensus | | cctgccTctTcaccccctGGggCcaagCAgaaaaTccagcTcaTaaac |

FIG. 1K-4

Alignment of HVR (aa) of HCV isolates of subtype 1a (I).

| SEQ ID NO | Isolate | | |
|---|---|---|---|
| 56 | DR4 | 1 | gTqvsGGSAaRTvnAlaglFdqGArQnIQLIN |
| 50 | S18 | 1 | DTYaTGGSAsRTtqAftrfFsPGAKQdIQLIN |
| 51 | S14 | 1 | DTYiTGGtAgRTvgtLsnLLaPGAKQNIQLIN |
| 55 | DK9 | 1 | DTrVTGGsAARntyGLaSLLsPGAKQNIQLIN |
| 52 | DK7 | 1 | sTHVTGGtAARAAfGiTSLFaPGAKQNIQLIs |
| 57 | DR1 | 1 | tTHVTGGSeARAASaLTGLFtrGArQNvQLIN |
| 53 | US11 | 1 | ETYVTGGSAGhAASGLaGLFsqGAQQNIQLIN |
| 54 | SW1 | 1 | ETYtTGGaAGqtASGftsLFtrGAQQNIQLvN |
| 50-57 | consensus | | dTyvtGGsaartasglt-lfspGAkQniQLin |

FIG. 2A

Alignment of HVR (aa) of HCV isolates of subtype 1b (II).

| SEQ ID NO | Isolate | | |
|---|---|---|---|
| 71 | S9 | 1 | gTtVTGAVQGRslQGltgLFSsGptQKlQLVN |
| 74 | DK1 | 1 | TTHVTGAVQGRTTQGfASLFSPGsaQKIQLVN |
| 64 | T3 | 1 | TTHVsGGVsARTThGLASfFSPGpSQKIQLVN |
| 61 | T10 | 1 | sTrVTGGTAARnTyGLASiFAPGaSQKIQLIN |
| 62 | HK5 | 1 | aThVTGGTAAHtTRGLTSLFAPGpSQKIQLIN |
| 72 | HK4 | 1 | nTYVTGGAAsHsTRGLTSLFTtGASQKIQLIN |
| 63 | HK8 | 1 | dTYVSGGAtaRnTyGLTSLFTPGAAQKIQLIN |
| 73 | S45 | 1 | GTYTSGqAaGRTTaGFTSiFnPGsAQsIQLIN |
| 66 | SA10 | 1 | GTYTtGgAqGRTTsSFvGlFtPGPSQrIQLvN |
| 70 | HK3 | 1 | sThTIGatvARTTQSwTGfFSsGPSQKIQLiN |
| 69 | IND8 | 1 | hTniIGGreAsTTQGFTSlFSpGaSQKIQLVN |
| 65 | SW2 | 1 | nTyTTGGeaAYnTRGFaSiFSSGpSQKIQLVN |
| 60 | P10 | 1 | rTHTTGGsvAYgTRrFTSLFTSGaSQKIQLVN |
| 67 | US6 | 1 | eTHvTGGaQAYaaRsFTSLFTPGsrQNIQLiN |
| 68 | IND5 | 1 | qakTIGGrQAhtTgrlVSMFTPGPSQNIQLVN |
| 59 | D1 | 1 | saspGTrTIGGsQAkhTssiVSMFSlGPSQKIQLVN |
| 58 | D3 | 1 | rggvGThTIGGaQAysvrgftSiFStGPaQKIQLVN |
| 58-74 | consensus | | ----gth-tGgaqarttrgftslFspGpsQkiQLvN |

Alignment of HVR (aa) of HCV isolates of genotype 1.

| SEQ ID NO | Isolate | | |
|---|---|---|---|
| 59 | D1 | 1 | saspGTrTIGGsQAkhtssivSmFSlGPsQKIQLVN |
| 58 | D3 | 1 | rggvGThTIGGaQAySvrGfTSiFStGPaQKIQLVN |
| 71 | S9 | 1 | GTtvtGAvQgRSlQGlTGlFSSGPtQKlQLVN |
| 70 | HK3 | 1 | sThTIGAtvARTTQswTGfFSSGPSQKIQLiN |
| 68 | IND5 | 1 | qakTIGGrqAhTTgrlvSmFtpGPSQnIQLVN |
| 65 | SW2 | 1 | nTyTTGGeaAYnTRgFaSiFsSGPSQKIQLVN |
| 60 | P10 | 1 | rThTTGGsvAYgTRrFTSLFtSGASQKIQLVN |
| 69 | IND8 | 1 | hTniiGGreAsTTqGFTSLFsPGASQKIQLVN |
| 73 | S45 | 1 | gTytsGqaaGRTTaGFTSiFnPGSAQsIQLiN |
| 74 | DK1 | 1 | TTHVtGaVqGRTTqGFASlFSPGSAQKIQLVN |
| 64 | T3 | 1 | TTHVSGGVsARTThGLASfFSPGpsQKIQLVN |
| 56 | DR4 | 1 | gTqVSGGSaARTvnALAGLFdqGARQNIQLIN |
| 57 | DR1 | 1 | tThVTGGSeARAASALtGLFtrGARQNvQLIN |
| 53 | US11 | 1 | eTyVTGGSAghAASGLAGLFSqGAqQNIQLIN |
| 55 | DK9 | 1 | dTRVTGGSAARNTYGLASLlSPGAkQNIQLIN |
| 61 | T10 | 1 | sTRVTGGtAARNTYGLASiFaPGAsQKIQLIN |
| 63 | HK8 | 1 | dTYVsGGAtARNTYGLTSLFTPGAaQKIQLIN |
| 72 | HK4 | 1 | nTYVTGGAAsHsTRGLTSLFTtGASQKIQLIN |
| 62 | HK5 | 1 | aTHVTGGTAAHtTRGLTSLFAPGpSQKIQLIN |
| 52 | DK7 | 1 | sTHVTGGTAArAAfGiTSLFAPGakQNIQLIs |
| 67 | US6 | 1 | ETHVTGGAqAyAArsFTSLFTPGsrQNIQLIN |
| 54 | SW1 | 1 | ETYTTGGAaGqTASgFTSLFTrGaqQNIQLVN |
| 66 | SA10 | 1 | gTYTTGGAqGRTTSsFvgLFTPGpsQrIQLVN |
| 50 | S18 | 1 | DTYaTGGsAsRTTqaFtrfFsPGAKQdIQLIN |
| 51 | S14 | 1 | DTYiTGGtAgRTvgtlsnllaPGAKQnIQLIN |
| 50-74 | consensus | | ----gt-vtGg-aarttrgltslfspGasQkiQLin |

FIGURE 2D

Alignment of HVR (aa) of HCV isolates of subtype 2a (III).

| SEQ ID NO | Isolate | | |
|---|---|---|---|
| 75 | US10 | 1 | aTrTvGhsAayTAstfagIFnaGsRQnIQLIn |
| 77 | T9 | 1 | tThTsGgtAghTAyGLTsIFSPGaRQkIQLIy |
| 76 | T4 | 1 | sstTiGSavasTTrGLTglFSPGsqQnIQLIN |
| 78 | T2 | 1 | hteltGSnagrTTqGLaafFtPGasQrvQLIN |
| 75-78 | consensus | | -t-t-Gs-a--T--gl-giFspG-rQniQLIn |

Alignment of HVR (aa) of HCV isolates of subtype 2b (IV).

| SEQ ID NO | Isolate | | |
|---|---|---|---|
| 80 | DK8 | 1 | aTYTTGgQaARdTwgLArLFspGaQQKlsLIN |
| 79 | T8 | 1 | tTYTTGAQvARTTASLAgLFttGPQQKINLIN |
| 81 | DK11 | 1 | nTrvTGAiagRTaASLAsLFnsGPQQKINLIN |
| 79-81 | consensus | | -TytTGaqaaRttasLA-LF--GpQQKinLIN |

FIG. 2E

Alignment of HVR (aa) of HCV isolates of genotype 2.

| SEQ ID NO | Isolate | | |
|---|---|---|---|
| 82 | S83 | 1 | tTytTGasAGqqvQsfArlFsPGpnQhVQLvr |
| 78 | T2 | 1 | hTelTGsnAGRtTQGLAafFtPGAsQrVQLIN |
| 80 | DK8 | 1 | aTYTTGgQAARdTwGLArLFsPGAQQKlsLIN |
| 79 | T8 | 1 | tTYTTGAQvARTTASLAgLFttGPQQKINLIN |
| 81 | DK11 | 1 | nTrvTGAiAGRTAASLASLFnsGPQQKINLIN |
| 77 | T9 | 1 | tThTsGgtAGhTAyGLTSiFSPGarQKIQLIy |
| 76 | T4 | 1 | sstTiGsavAsTtrGLTGlFSPGSqQNIQLIN |
| 75 | US10 | 1 | atrTvGhsaAyTastfaGiFnaGSrQNIQLIN |
| 75-82 | consensus | | ttyttGa-a-rtt-glaglFspG-qQkiqLin |

FIG. 2F

Alignment of HVR (aa) of HCV isolates of subtype 3a (V).

| SEQ ID NO | Isolate | | |
|---|---|---|---|
| 83 | HK10 | 1 | gTYisGGhvARgASgLASFFSPGAkQnLQLiN |
| 84 | S2 | 1 | ETYVTGGSaARSASrLASFFSPGAqQKLQLVN |
| 85 | S52 | 1 | ETYVTGGSvAHSArGLTSLFSmGAKQKLQLVN |
| 86 | S54 | 1 | aTYtTGGSAAHSAqGiTrLFSVGAKQnLQLVN |
| 87 | DK12 | 1 | tThvTGGdAArStlrfTsLFSVGsnQqLQLVN |
| 83-87 | consensus | | eTyvtGGsaArsasgltslFS-GakQ-LQLvN |

FIG. 2G

Alignment of HVR (aa) of HCV isolates of subtype 4c.

| SEQ ID NO | Isolate | | |
|---|---|---|---|
| 90 | Z7 | 1 | tTmTTGGaaARtahAfTgLFtSGPqQkLQLIN |
| 91 | Z6 | 1 | eTvTTGGsvARstrAiTsLFnSGPkQnLQLIN |
| 90-91 | consensus | | -T-TTGG--AR---A-T-LF-SGP-Q-LQLIN |

FIG. 2H

Alignment of HVR (aa) of HCV isolates of genotype 4.

| SEQ ID NO | Isolate | | |
|---|---|---|---|
| 89 | Z1 | 1 | tTYasGaaAGrTtsgfaGLFTpGakQNIrLIN |
| 92 | DK13 | 1 | gTYvTGGqAGqTAfhlTGLFTrGshQNIQLIN |
| 90 | Z7 | 1 | tTmTTGGaAARTAhAfTGLFTSGPqQkLQLIN |
| 91 | Z6 | 1 | eTvTTGGsvARstrAiTSLFnSGPkQNLQLIN |
| 88 | Z4 | 1 | hTsvsGGtqARaaqglTSLFtSGPrQNLQLIN |
| 88-92 | consensus | | tTy-tGgaaarta---tgLFtsGpkQnlqLIN |

FIG. 2I

Alignment of HVR (aa) of HCV isolates of subtype 5a.

| SEQ ID NO | Isolate | | |
|---|---|---|---|
| 93 | SA6 | 1 | sTHsVgGsAAhtTsGFtSlFnPGPKQNLQLIy |
| 94 | SA1 | 1 | rTHTVaGtAAysTRGFASiFTPGPKQNLQLIN |
| 95 | SA13 | 1 | NTrTVGGsAAqgARGlASLFTPGPqQNLQLIN |
| 97 | SA7 | 1 | NTHvVGGaAArsAsGmASLFTvGAkQNLQLIN |
| 96 | SA4 | 1 | NTHisGGtAAktvqGftSLFsfGAqQNLQLIN |
| 93-97 | consensus | | nThtvgG-AA----GfaSlFtpGpkQNLQLIn |

FIG. 2J

Alignment of HVR (aa) of 49 HCV isolates of genotypes 1-6.

| SEQ ID NO | Isolate | | |
|---|---|---|---|
| 71 | S9 | 1 | gTtVTGavqgRSlqglTgLFSsGptQkLQLVN |
| 87 | DK12 | 1 | TThVTGgdAaRStlrFTsLFSvGsNQqLQLVN |
| 82 | S83 | 1 | TTyTTGasAGqqvqSFArLFSPGpNQhvQLVr |
| 98 | HK2 | 1 | TTTTGhAVGrTTsSLAGLFSPGakQNlQLIN |
| 76 | T4 | 1 | SsTTIGsAVAsTTrgLTGLFSPGsqQNIQLIN |
| 70 | HK3 | 1 | SThTIGatVARTTQswTGFFSsGpSQkIQLIN |
| 78 | T2 | 1 | hTelTGsnAgRTTQglaaFFtPGASQrvQLIN |
| 50 | S18 | 1 | DTYaTGGsAsRTTQaftrFFsPGAKQdIQLIN |
| 51 | S14 | 1 | DTYiTGGtAgRTVgtLsnLlaPGAKQNIQLIN |
| 56 | DR4 | 1 | GTqVsGGsAaRTVnaLaGLFdqGArQNIQLIN |
| 92 | DK13 | 1 | GTyVTGGqAgqTAfhLTGLFTrGshQNIQLIN |
| 90 | Z7 | 1 | tTmTTGGAAarTAhaFTGLFTsGpQQklQLIN |
| 54 | SW1 | 1 | ETYTTGGAAGqTASGFTsLFTrGAQQNIQLvN |
| 53 | US11 | 1 | ETYVTGGSAGhaASGLAgLFSqGAQQNIQLIN |
| 55 | DK9 | 1 | dTRVTGGSAARNTYGLASLlSPGAkQNIQLIN |
| 61 | T10 | 1 | sTRVTGGtAARNTYGLASiFaPGAsQKIQLIN |
| 63 | HK8 | 1 | dTYVsGGAtARNTYGLTSLFTPGAaQKIQLIN |
| 72 | HK4 | 1 | nTYVTGGAAsHsTRGLTSLFTtGASQKIQLIN |
| 62 | HK5 | 1 | aTHVTGGTAAHtTRGLTSLFAPGpSQKIQLIN |
| 52 | DK7 | 1 | sTHVTGGTAARaAfGiTSLFAPGAKQNIQLIs |
| 97 | SA7 | 1 | NTHVVGGaAARsAsGmASLFTvGAKQNLQLIN |
| 95 | SA13 | 1 | NTrtVGGsAAqgArGLASLFTpGPqQNLQLIN |
| 88 | Z4 | 1 | hTsVsGGtqARAAqGLTSLFTsGPRQNLQLIN |
| 57 | DR1 | 1 | tTHVTGGseARAAsaLTgLFTrGaRQNvQLIN |
| 67 | US6 | 1 | eTHVTGGaqAYAARsFTSLFTpGsRQNIQLIN |
| 60 | P10 | 1 | rTHTTGGSVAYgTRrFTSLFTSGasQkIQLvN |
| 91 | Z6 | 1 | ETvTTGGSVArSTRaiTSLFnSGpKQnLQLiN |
| 85 | S52 | 1 | ETYvTGGSVAHSARGlTSLFSmGAKQkLQLVN |
| 86 | S54 | 1 | ATYTTGGSAAHSAqGiTRLFSvGAKQnLQLVN |
| 80 | DK8 | 1 | ATYTTGGQAARdTwGLARLFSpGAQQKLsLIN |
| 79 | T8 | 1 | tTYTTGAQvARTTASLAgLFttGPQQKINLIN |
| 81 | DK11 | 1 | nTrVTGAiAgRTAASLASLFnsGPQQKINLIN |
| 84 | S2 | 1 | eTYVTGGsAARsASrLASFFSPGAQQKLQLvN |
| 83 | HK10 | 1 | gTYISGGhvARgASGLASFFSPGAkQNLQLIN |
| 96 | SA4 | 1 | nThISGGtaAkTvQGFTSLFSfGAqQNLQLIN |
| 69 | IND8 | 1 | hTnIiGGreAsTTQGFTSLFSPGAsQKIQLVN |
| 74 | DK1 | 1 | TTHVtGaVqgRTTQGFASLFSPGsaQKIQLVN |
| 64 | T3 | 1 | TTHVsGGVsARTThGlASfFSPGPSQKIQLVN |
| 65 | SW2 | 1 | nTYTTGGeaAynTrGFASiFSsGPSQKIQLVN |
| 66 | SA10 | 1 | gTYTTGGAqGRTTSsFvGLFTPGPSQrIQLVN |
| 89 | Z1 | 1 | tTYaSGaAAGRTTSGFaGLFTPGakQnIrLIN |
| 73 | S45 | 1 | gTYTSGqAAGRTTaGFTSIFnPGsaQsIQLIN |
| 77 | T9 | 1 | tTHTSGGtAGHTayGlTSIFsPGarQkIQLIY |
| 93 | SA6 | 1 | sTHsVGGsAAHTTsGFTSlFnPGPKQNLQLIY |

FIG. 2K-1

| | | | |
|---|---|---|---|
| 94 | SA1 | 1 | rTHTVaGtAAYsTrGFASIFtPGPKQNLQLIN |
| 75 | US10 | 1 | aTrTVGhsAAYTastFAgIFnaGsrQNIQLIN |
| 68 | IND5 | 1 | qakTIGGrQAhTTgrlVSMFtpGPSQNIQLVN |
| 59 | D1 | 1 | saspGTrTIGGsQAkhTssiVSMFSlGPSQKIQLVN |
| 58 | D3 | 1 | rggvGThTIGGaQAysvrgftSiFStGPaQKIQLVN |
| 50-98 | consensus | | ----ttyttggsaarttsgltslfspGakQniqLin |

FIG. 2K-2

NUCLEOTIDE AND DEDUCED AMINO ACID SEQUENCES OF HYPERVARIABLE REGION 1 OF THE ENVELOPE 2 GENE OF ISOLATES OF HEPATITIS C VIRUS AND THE USE OF REAGENTS DERIVED FROM THESE HYPERVARIABLE SEQUENCES IN DIAGNOSTIC METHODS AND VACCINES

FIELD OF INVENTION

The present invention is in the field of hepatitis virology. The invention relates to the nucleotide and deduced amino acid sequences of hypervariable region 1 of the envelope 2 (E2) gene of hepatitis C virus (HCV) isolates from around the world and the grouping of these hypervariable sequences into distinct HCV genotypes. More specifically, this invention relates to diagnostic methods and vaccines which employ nucleic acid sequences and recombinant or synthetic proteins derived from these hypervariable sequences.

BACKGROUND OF INVENTION

Hepatitis C, originally called non-A, non-B hepatitis, was first described in 1975 as a disease serologically distinct from hepatitis A and hepatitis B (Feinstone, S. M. et al. (1975) *N. Engl. J. Med.*, 292:767–770). Although hepatitis C was (and is) the leading type of transfusion-associated hepatitis as well as an important part of community-acquired hepatitis, little progress was made in understanding the disease until the recent identification of hepatitis C virus (HCV) as the causative agent of hepatitis C via the cloning and sequencing of the HCV genome (Choo, A. L. et al. (1989) *Science*, 288:359–362). The sequence information generated by this study resulted in the characterization of HCV as a small, enveloped, positive-stranded RNA virus and led to the demonstration that HCV is a major cause of both acute and chronic hepatitis worldwide (Weiner, A. J. et al. (1990) *Lancet*, 335:1–3). Subsequently, it has been observed that approximately 80% of individuals acutely infected with HCV become chronically infected and more than 20% of these individuals eventually develop liver cirrhosis (Alter, H. J. Seeff, L. B.: Transfusion Associated Hepatitis, In: Zuckerman, A. J. Thomas, H. C. (eds): Viral Hepatitis: Scientific Basis and Clinical Management. Edinburgh Churchill Livingstone, 1993). In addition, a strong association has been found between HCV infection and the development of hepatocellular carcinoma (Bukh et al. (1993) *Proc. Natl. Acad. Sci. USA*, 90:1848–1851) and HCV infection also seems to be associated with other diseases, including some autoimmune diseases (Manns, M. P. (1993) *Intervirol.*, 35:108–115; Lionel, F. (1994) *Gastroenterology*, 107:1550–1555). Thus, significant morbidity and mortality is caused by HCV infection worldwide and vaccine development is a high priority.

Choo et al. ((1994) *Proc. Natl. Acad. Sci. USA*, 91:1294–1298), using recombinant E1 and E2 proteins of HCV-1 as immunogens, reported the successful vaccination of chimpanzees against challenge with $10CID_{50}$ of the homologous strain of HCV. However, Choo et al. did not demonstrate protection against challenge with a heterologous strain of HCV and the recent discovery of the extraordinary diversity of HCV genomes based on sequence analysis of numerous HCV isolates (Bukh et al.; *Proc. Natl. Acad. Sci. USA*, (1993) 90:8234–8238, Bukh et al. (1994) *Proc. Natl. Acad. Sci. USA*, 91:8239–8243) suggests that a successful vaccine must protect against challenge by multiple strains of HCV. In addition, both Farci et al. (Farci, P. et al. (1992) *Science*, 258:135–140) and Prince et al. (Prince, A. M. et al. (1992) *J. Infect. Dis.*, 165:438–443) have presented evidence that while infection with one strain of HCV does modify the degree of the hepatitis C associated with the reinfection, it does not protect against reinfection with a closely related strain.

One possible candidate for use as a immunogen in a vaccine protective against multiple strains of HCV is a short region within the E2 gene termed hypervariable region 1 (HVR1) that has many similarities to the V3 loop of HIV, which represents the principal neutralizing domain of HIV (Letvin, N. L. (1993) *N. Engl. J. Med.*, 329:1400). Indeed, the recent demonstration that antibodies specific to HVR1 can neutralize HCV in an in vitro binding assay (Zibert, A. et al. (1995) *Virology*, 208:653–661) suggests that HVR1 may be a principal neutralization determinant of HCV. Thus, the identification of HVR1 sequences from multiple HCV isolates of different genotypes may be useful in developing an immunogen capable of stimulating a protective immune response against challenge by infection with HCV isolates.

SUMMARY OF INVENTION

The present invention relates to the nucleotide and deduced amino acid sequences of hypervariable region 1 (HVR1) of the envelope 2 (E2) gene of 49 human hepatitis C virus (HCV) isolates.

The invention also relates to proteins derived from the hypervariable sequences disclosed herein. These proteins may be synthesized chemically or may be produced recombinantly by inserting hypervariable nucleic acid sequences into an expression vector and expressing the recombinant protein in a host cell.

The invention further relates to the use of these proteins, either alone, or in combination with each other, as diagnostic agents and as vaccines.

The invention further relates to the use of expression vectors containing the hypervariable nucleic acid sequences of the present invention as nucleic acid based vaccines.

This invention therefore relates to pharmaceutical compositions useful in prevention or treatment of hepatitis C in a mammal.

The invention also relates to the use of single-stranded antisense poly- or oligonucleotides derived from HVR1 nucleic acid sequences to inhibit expression of hepatitis C E2 genes.

The invention further relates to multiple computer-generated alignments of the nucleotide and deduced amino acid sequences of the HVR1 sequences. These multiple sequence alignments produce consensus sequences which serve to highlight regions of homology and non-homology between sequences found within the same genotype or in different genotypes and hence, these alignments can be used by those of ordinary skill in the art to design proteins and nucleic acid sequences useful as reagents in diagnostic assays and vaccines.

The present invention also encompasses methods of detecting antibodies specific for hepatitis C virus in biological samples. The methods of detecting HCV or antibodies to HCV disclosed in the present invention are useful for diagnosis of infection and disease caused by HCV and for monitoring the progression of such disease. Such methods are also useful for monitoring the efficacy of therapeutic agents during the course of treatment of HCV infection and disease in a mammal.

The invention also provides a kit for the detection of antibodies specific for HCV in a biological sample where said kit contains at least one purified and isolated protein derived from the hypervariable sequences.

The invention also relates to methods for detecting the presence of hepatitis C virus in a mammal, said methods comprising analyzing the RNA of a mammal for the presence of hepatitis C virus. These methods can be used to identify specific isolates of hepatitis C virus present in a mammal which is useful in determining the proper course of treatment for an HCV-infected patient.

The invention also provides a diagnostic kit for the detection of hepatitis C virus in a biological sample. The kit comprises purified and isolated nucleic acid sequences useful as primers for reverse-transcription polymerase chain reaction (RT-PCR) analysis of RNA for the presence of hepatitis C virus genomic RNA.

The invention also relates to antibodies to the HVR1 proteins of the present invention and the use of such antibodies in passive immunoprophylaxis.

DESCRIPTION OF FIGURES

FIGS. 1A–K show computer generated sequence alignments of the nucleotide sequences of the HVR1 region of the E2 gene of 49 HCV isolates. The single letter abbreviations used for the nucleotides shown in FIGS. 1A–K are those standardly used in the art. FIG. 1A shows the alignment of SEQ ID NOs:1–8 to produce a consensus sequence for subtype I/1a. FIGS. 1B-1 and 1B-2 show the alignment of SEQ ID NOs:9–25 to produce a consensus sequence for subtype II/1b. FIGS. 1C-1, 1C-2 and 1C-3 show the alignment of SEQ ID NOs:1–25 to produce a consensus for genotype 1 where genotype 1 comprises subtypes 1a (SEQ ID NOs:1–8) and 1b (SEQ ID NOs:9–25). FIG. 1D shows the alignment of SEQ ID NOs:26–29 to produce a consensus sequence for subtype III/2a. FIG. 1E shows the alignment of SEQ ID NOs:30–32 to produce a consensus sequence for subtype IV/2b. FIG. 1F shows the alignment of SEQ ID NOs:26–33 to produce a consensus sequence for genotype 2 where genotype 2 comprises subtypes 2a (SEQ ID NOs:26–29), 2b (SEQ ID NOs:30–32) and 2c (SEQ ID NO:33). FIG. 1G shows the alignment of SEQ ID NOs:34–38 to produce a consensus sequence for genotype V/3a. FIG. 1H shows the computer alignment of SEQ ID NOs:41–42 to produce a consensus sequence for subtype 4c. FIG. 1I shows the alignment of SEQ ID NOs: 39–43 to produce a consensus sequence for genotype 4 where genotype 4 comprises subtypes 4a (SEQ ID NO:39), 4b (SEQ ID NO:40), 4c (SEQ ID NOs:41–42) and 4d (SEQ ID NO:43). FIG. 1J shows the alignment of SEQ ID NOs:44–48 to produce a consensus sequence for genotype 5a. FIGS. 1K-1 and 1K-4 show the alignment of the HVR1 sequences of the 49 HCV isolates (SEQ ID NOs: 1–49) to produce a consensus sequence for all genotypes. The nucleotides shown in capital letters in the consensus sequences of FIGS. 1A–1K are those conserved within a genotype (FIGS. 1A–J) or among all isolates (FIGS. 1K-1 and 1K-4) while nucleotides shown in lower case letters in the consensus sequences are those variable within a genotype (FIGS. 1A–J) or among all isolates (FIGS. 1K-1–1K-4). In addition, when the lower case letter is shown in a consensus sequence, the lower case letter represents the nucleotide found most frequently in the sequences aligned to produce the consensus sequence. Finally, a hyphen at a nucleotide position in the consensus sequences in FIGS. 1A–K indicates that two nucleotides were found in equal numbers at that position in the aligned sequences. In the aligned sequences, nucleotides are shown in lower case letters if they differed from the nucleotides of both adjacent isolates.

FIGS. 2A–K show computer alignments of the deduced amino acid sequences of amino acid sequences of the HVR1 region of the envelope 2 gene of 49 isolates of HCV. The single letter abbreviations used for the amino acids shown in FIGS. 2A–K follow the conventional amino acid shorthand for the twenty naturally occurring amino acids. FIG. 2A shows the alignment of SEQ ID NOs:50–57 to produce a consensus sequence for subtype I/1a. FIG. 2B shows the alignment of SEQ ID NOs:58–74 to produce a consensus sequence for subtype II/1b. FIGS. 2C shows the alignment of SEQ ID NOs:50–74 to produce a consensus sequence for genotype 1 where genotype 1 comprises subtypes 1a (SEQ ID NOs:50–57) and 1b (SEQ ID NOs:58–74). FIG. 2D shows the alignment of SEQ ID NOs:75–78 to produce a consensus sequence for subtype III/2a. FIG. 2E shows the alignment of SEQ ID NOs:79–81 to produce a consensus sequence for subtype IV/2b. FIG. 2F shows the alignment of SEQ ID NOs:75–82 to produce a consensus sequence for genotype 2 where genotype 2 comprises subtypes 2a (SEQ ID NOs:75–78), 2b (SEQ ID NOs:79–81) and 2c (SEQ ID NO:82). FIG. 2G shows the alignment of SEQ ID NOs:83–87 to produce a consensus sequence for genotype V/3a. FIG. 2H shows the computer alignment of SEQ ID NOs:90–91 to produce a consensus sequence for subtype 4c. FIG. 2I shows the alignment of SEQ ID NOs:88–92 to produce a consensus sequence for genotype 4 where genotype 4 comprises subtypes 4a (SEQ ID NO:88), 4b (SEQ ID NO:89), 4c (SEQ ID NOs:90–91) and 4d (SEQ ID NO:92). FIG. 2J shows the alignment of SEQ ID NOs:93–97 to produce a consensus sequence for genotype 5a. FIGS. 2K-1 and 2K-2 shows the alignment of the HVR1 amino acid sequences of the 49 HCV isolates (SEQ ID NOs: 50–98) to produce a consensus sequence for all genotypes. The amino acids shown in capital letters in the consensus sequences of FIGS. 2A–K are those conserved within a genotype (FIGS. 2A–J) or among all isolates (FIG. 2K) while amino acids shown in lower case letters in the consensus sequences are those variable within a genotype (FIGS. 2A–J) or among all isolates (FIGS. 2K-1 and 2K-2). In addition, when the lower case letter is shown in a consensus sequence, the letter represents the amino acid found most frequently in the sequences aligned to produce the consensus sequence. Finally, a hyphen at an amino acid position in the consensus sequences of FIGS. 2A–K indicates that two amino acids were found in equal numbers at that position in the aligned sequences. In the aligned sequences, amino acids are shown in lower case letters if they differed from the amino acids of both adjacent isolates.

DETAILED DESCRIPTION OF INVENTION

The present invention relates to nucleotide and deduced amino acid sequences of hypervariable region 1 (HVR1) of the E2 gene of 49 isolates of human hepatitis C virus (HCV) where HVR1 is defined as starting at amino acid 384 of the HCV polyprotein (Bukh, J. et al. (1995) *Seminars in Liver Disease*, 15: 41–63; Hijikata, M. et al. (1991) *Biochem. Biophys. Res. Comm.*, 175: 220–228; and Hijikata, M. et al. (1991) *Proc. Natl. Acad. Sci. U.S.A.*, 88: 5547–5551) The nucleic acid sequences of the present invention were obtained as follows. Viral RNA was extracted from serum collected from humans infected with hepatitis C virus and the viral RNA was then reverse transcribed and amplified by polymerase chain reaction using primers deduced from the sequence of the HCV strain H-77 (Bukh, et al. (1993) *Proc. Natl. Acad. Sci. U.S.A.*, 90:8234–8238). The amplified cDNA was then isolated by gel electrophoresis and sequenced.

The HVR1 nucleotide sequences of the 49 HCV isolates are shown in the sequence listing as SEQ ID NO:1 through SEQ ID NO:49.

The abbreviations used for the nucleotides are those standardly used in the art.

The deduced amino acid sequence of each of SEQ ID NO:1 through SEQ ID NO:49 are presented in the sequence listing as SEQ ID NO:50 through SEQ ID NO:98 where the amino acid sequence in SEQ ID NO:50 is deduced from the nucleotide sequence shown in SEQ ID NO:1, the amino acid sequence shown in SEQ ID NO:51 is deduced from the nucleotide sequence shown in SEQ ID NO:2 and so on. The deduced amino acid sequence of each of SEQ ID Nos:50–98 starts at nucleotide 1 of the corresponding nucleic acid sequence shown in SEQ ID NOs:1–49.

The three letter abbreviations used in SEQ ID NOs:50–98 follow the conventional amino acid shorthand for the twenty naturally occurring amino acids.

Preferably, the HVR1 proteins of the present invention are substantially homologous to, and most preferably biologically equivalent to, native HCV HVR1 proteins. For purposes of the present invention, protein as used herein refers to a molecule containing a complete amino acid sequence shown in SEQ ID NOs 50–98 or a fragment of these sequences of at least about 6 to about 8 amino acids in length. By "biologically equivalent" as used throughout the specification and claims, it is meant that the compositions are immunogenically equivalent to the native HVR1 proteins. The HVR1 proteins of the present invention may also stimulate the production of protective antibodies upon injection into a mammal that would serve to protect the mammal upon challenge with HCV. By "substantially homologous" as used throughout the ensuing specification and claims to describe HVR1 proteins, it is meant a degree of homology in the amino acid sequence of the HVR1 proteins to the native HVR1 amino acid sequences disclosed herein. Preferably the degree of homology is in excess of 80%, preferably in excess of 90%, with a particularly preferred group of proteins being in excess of 95% homologous with the native HVR1 amino acid sequences.

Variations are contemplated in the nucleic acid sequences shown in SEQ ID NO:1 through SEQ ID NO:49 which will result in a nucleic acid sequence that is capable of directing production of a protein having at least six contiguous amino acids shown in SEQ ID NO:50 through SEQ ID NO:98 or an analog thereof. Due to the degeneracy of the genetic code, it is to be understood that numerous choices of nucleotides may be made that will lead to a DNA sequence capable of directing production of the instant protein or its analogs. As such, DNA sequences which are functionally equivalent to the sequences set forth above or which are functionally equivalent to sequences that would direct production of HVR1 amino acid sequences set forth in SEQ ID NOs:50–98 or analog thereof are intended to be encompassed within the present invention.

The term analog as used throughout the specification or claims to describe the HVR1 proteins of the present invention, includes any protein having an amino acid residue sequence substantially identical to a sequence specifically shown herein in which one or more residues have been conservatively substituted with a biologically equivalent residue. Examples of conservative substitutions include the substitution of one polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that the resulting protein is biologically equivalent to the native HVR1 protein.

"Chemical derivative" refers to an HVR1 protein having one or more residues chemically derivatized by reaction of a functional side group. Examples of such derivatized molecules, include but are not limited to, those molecules in which free amino groups have been derivatized to form amine hydrochlorides, p-toluene sulfonyl groups, carbobenzoxy groups, t-butyloxycarbonyl groups, chloracetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imbenzylhistidine. Also included as chemical derivatives are those proteins which contain one or more naturally-occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. The HVR1 proteins of the present invention also include any protein having one or more additions and/or deletions of residues relative to the sequence of a peptide whose sequence is shown herein, so long as the protein is biologically equivalent to the native HVR1 protein.

The present invention also relates to multiple computer-generated alignments of the nucleotide and deduced amino acid sequences shown in SEQ ID NOs:1–98.

The grouping of SEQ ID NOs:1–49 into HCV genotypes is shown below.

| SEQ ID NOs: | Subtypes | Genotypes |
|---|---|---|
| 1–8 | I/1a | 1 |
| 9–25 | II/1b | |
| 26–29 | III/2a | 2 |
| 30–32 | IV/2b | |
| 33 | 2c | |
| 34–38 | V/3a | 3 |
| 39 | 4a | 4 |
| 40 | 4b | |
| 41–42 | 4c | |
| 43 | 4d | |
| 44–48 | 5a | 5 |
| 49 | 6a | 6 |

For those subtypes or genotypes containing more than one HVR1 nucleotide sequence, computer alignment of the constituent nucleotide sequences of the subtype or genotype was conducted using the program GENALIGN (Intelligenetics Inc. Mountainview, Calif.) in order to produce a consensus sequence. These alignments and their resultant consensus sequences are shown in FIGS. 1A–1J. Further alignment of the sequences of all 49 HVR1 sequences to produce a consensus sequence for all genotypes is shown in FIGS. 1K-1–1K-4. The consensus sequences shown in FIGS. 1A–K serve to highlight regions of homology and non-homology between sequences found within the same subtype or genotype or in different genotypes and hence, these alignments can be used by one skilled in the art to select HVR1 sequences useful as reagents in diagnostic assays or vaccines.

The grouping of SEQ ID NOs:50–98 into HCV genotypes is shown below:

| SEQ ID NOs: | Subtypes | Genotypes |
|---|---|---|
| 50–57 | I/1a | 1 |
| 58–74 | II/1b | |
| 75–78 | III/2a | 2 |
| 79–81 | IV/2b | |
| 82 | 2c | |
| 83–87 | V/3a | 3 |
| 88 | 4a | 4 |
| 89 | 4b | |
| 90–91 | 4c | |
| 92 | 4d | |
| 93–97 | 5a | 5 |
| 98 | 6a | 6 |

For those subtypes or genotypes containing more than one HVR1 amino acid sequence, computer alignment of the constituent sequences of each subtype or genotype was conducted using the computer program GENALIGN in order to produce a consensus sequence. These alignments and their resultant consensus sequences are shown in FIGS. 2A–J. Alignment of all 49 HVR1 sequences to produce a consensus amino acid sequence for all genotypes is shown in FIGS. 2K-1 and 2K-2. The consensus sequences shown in FIGS. 2A–2K serve to highlight regions of homology and non-homology between HVR1 amino acid sequences of the same subtype or genotype and of different genotypes and hence, these alignments can readily be used by those skilled in the art to design HVR1 proteins useful in assays and vaccines for the diagnosis and prevention of HCV infection.

In order to identify hydrophilic domains within HVR1 that might represent antigenic determinants, a Kyte and Doolittle analysis (Kyte, J. and Doolittle, R. F. (1982) *J. Mol. Biol.*, 157:105–132) of each of the amino acid sequences shown in SEQ ID NOS:50–98 was conducted. The observed hydrophilic domains for the amino acid sequences of each of these isolates is shown below where amino acid position 1 is the amino-terminal amino acid of the HVR1 amino acid sequences shown in SEQ ID NOs:50–98. (Note that all the amino acid sequences shown in SEQ ID NOs: 50–98 are 32 amino acids in length except for SEQ ID NOs 58 and 59 (isolates D1 and D3 respectively) which are 36 amino acids in length due to the presence of an additional four amino acids in their amino termini and SEQ ID NO 98 which is lacking a single amino terminal amino acid relative to SEQ ID NOs: 50–57 and 60–97 and five amino terminal amino acids relative to SEQ ID NOs 58 and 59. Thus in the table below, the first four amino acids of SEQ ID NOs 58 and 59 are represented by the numbers −4, −3, −2 and −1 while the first amino acid in SEQ ID NO: 98 (isolate HK2) is assigned the number 2).

| Type | Isolate | amino acid position of HVR 5→3 | | | |
|---|---|---|---|---|---|
| 6a | HK2 | 2–6 | | 9–13 | 23–28 |
| 5a | SA6 | 1–5 | | 9–14 | 22–28 |
| 5a | SA13 | 1–5 | | 9–13 | 22–28 |
| 5a | SA1 | 1–4 | | 11–15 | 22–28 |
| 5a | SA7 | 1–2 | | 11–14 | 23–28 |
| 5a | SA4 | 1–5 | | 9–13 | 23–28 |
| 4c | Z6 | 1–4 | | 9–15 | 22–28 |
| 4b | Z1 | 1–4 | | 9–14 | 23–28 |
| 4a | Z4 | 1–4 | | 7–13 | 22–28 |
| 3a | S2 | 1–5 | | 9–14 | 23–28 |
| 3a | S52 | 1–5 | | 12–15 | 23–28 |
| 2c | S83 | 1–5 | | 9–15 | 22–28 |
| 2b | T8 | 1–6 | | 9–13 | 22–28 |
| 1b | T3 | 1–4 | | 11–14 | 23–28 |
| 1b | HK4 | 1–4 | | 9–16 | 23–28 |
| 1b | HK3 | 1–4 | | 10–16 | 23–28 |
| 1b | S9 | 1–2 | | 8–14 | 23–28 |
| 1b | IND8 | 1–2 | | 7–16 | 23–28 |
| 1b | T10 | 1–5 | | 9–14 | 23–28 |
| 1b | DK1 | 1–3 | | 8–14 | 23–28 |
| 1b | P10 | 1–6 | | 12–16 | 23–28 |
| 1a | S18 | 1–5 | | 8–16 | 23–28 |
| 1a | SW1 | 1–5 | | 9–13 | 23–28 |
| 1a | S14 | 1–3 | | 8–13 | 23–28 |
| 1a | US11 | 1–4 | | 8–10 | 23–28 |
| 3a | S54 | 1–6 | | 9–16 | 23–28 |
| 1b | IND5 | | 1–14 | | 22–28 |
| 1a | DR1 | | 1–12 | | 22–28 |
| 1b | D3 | −4→1 | | 9–13 | 23–28 |
| 1b | HK8 | 1–4 | | 9–15 | 23–28 |
| 1a | DK9 | 1–5 | | 9–14 | 23–28 |
| 1b | SA10 | | 1–13 | | 23–28 |
| 1b | S45 | | 1–13 | | 23–27 |
| 1b | D1 | | −4–14 | | 23–28 |
| 1b | SW2 | | 1–15 | | 23–28 |
| 2a | T2 | | 1–14 | | 23–28 |
| 2a | T9 | | 1–13 | | 23–28 |
| 2b | DK8 | | 1–14 | | 23–28 |
| 1a | DK7 | 1–5 | | 8–9 | 23–28 |
| 1a | DR4 | 1–5 | | 9–12 | 22–28 |
| 1b | US6 | 1–4 | | 8–16 | 22–28 |
| 1b | HK5 | 1–2 | | 9–16 | 23–28 |
| 2a | T4 | 1–2 | | 12–15 | 23–28 |
| 2a | US10 | 1–6 | | 9–10 | 23–28 |
| 3a | HK10 | | | 9–13 | 23–28 |
| 4d | DK13 | | | 7–13 | 22–28 |
| 4c | Z7 | | | 12–13 | 23–28 |
| 3a | DK12 | | 1–14 | | 23–28 |
| 2b | DK11 | 1–4 | | 12–13 | 22–28 |

The data presented above illustrate that there are typically 3 hydrophilic domains present in the HVR1 amino acid sequences shown in SEQ ID NOs:50–98. These hydrophilic domains are located at the amino and carboxy termini of HVR1 and in roughly the middle of HVR1. Although all three of these hydrophilic domains may represent important antigenic determinants, the carboxy terminal hydrophilic domain of about 6 amino acids in length is of particular interest in that it is universally conserved in the amino acid sequences shown in SEQ. ID NOs:50–98. This conservation of the C-terminal hydrophilic domain suggests that this domain may not only be an immunodominant epitope for HCV but may also play an important role in the viral life cycle. Thus, amino acid sequences containing the C-terminal hydrophilic domains of SEQ ID NOs:50–98 are preferred immunogens in the vaccines of the present invention.

Accordingly, the present invention includes a recombinant DNA method for the manufacture of HVR1 proteins in which natural or synthetic nucleic acid sequences may be used to direct the production of HVR1 proteins having at least six contiguous amino acids contained in the amino acid sequences shown in SEQ ID NOs:50–98.

In one embodiment of the invention, the method comprises:

(a) preparation of a nucleic acid sequence capable of directing a host organism to produce HVR1 protein;

(b) cloning the nucleic acid sequence into a vector capable of being transferred into and replicated in a host organism, such vector containing operational elements for the nucleic acid sequence;

(c) transferring the vector containing the nucleic acid and operational elements into a host organism capable of expressing the protein;

(d) culturing the host organism under conditions appropriate for amplification of the vector and expression of the protein; and (e) harvesting the protein.

In another embodiment of the invention, the method for the recombinant DNA synthesis of an HCV HVR1 protein encoded by any one of the nucleic acid sequences shown in SEQ ID NOs:1–49 comprises:

(a) culturing a transformed or transfected host organism containing a nucleic acid sequence capable of directing the host organism to produce HVR1 protein, under conditions such that the protein is produced, said protein exhibiting substantial homology to a native HVR1 protein having an amino acid sequence according to any one of the amino acid sequences shown in SEQ ID NOs:50–98.

In one embodiment, the RNA sequence of an HCV isolate was isolated and converted to cDNA as follows. Viral RNA was extracted from a biological sample collected from human subjects infected with hepatitis C and the viral RNA is then reverse transcribed and amplified by polymerase chain reaction using primers deduced from the sequence of HCV strain H-77 as described in Bukh et al. ((1993) *Proc. Natl. Acad. Sci. USA*, 90:8234–8238). Once amplified, the PCR fragments are isolated by gel electrophoresis and sequenced. This approach was used to obtain the nucleic acid sequences shown in SEQ ID NOs:1–49. In an alternative embodiment, a nucleic acid sequence capable of directing host organism synthesis of the given HVR1 protein may be synthesized chemically and inserted into an expression vector.

The vectors contemplated for use in the present invention include any vectors into which a nucleic acid sequence as described above can be inserted, along with any preferred or required operational elements, and which vector can then be subsequently transferred into a host organism and replicated in such organisms. Preferred vectors are those whose restriction sites have been well documented and which contain the operational elements preferred or required for transcription of the nucleic acid sequence.

The "operational elements" as discussed herein include at least one promoter, at least one operator, at least one leader sequence, at least one terminator codon, and any other DNA sequences necessary or preferred for appropriate transcription and subsequent translation of the vector nucleic acid. In particular, it is contemplated that such vectors will contain at least one origin of replication recognized by the host organism along with at least one selectable marker and at least one promoter sequence capable of initiating transcription of the nucleic acid sequence.

In construction of the recombinant expression vectors of the present invention, it should additionally be noted that multiple copies of the nucleic acid sequence of interest and its attendant operational elements may be inserted into each vector. In such an embodiment, the host organism would produce greater amounts per vector of the desired HVR1 protein. The number of multiple copies of the nucleic acid sequence which may be inserted into the vector is limited only by the ability of the resultant vector due to its size, to be transferred into and replicated and transcribed in an appropriate host microorganism.

Of course, those of ordinary skill in the art would readily understand that multiple copies of different HVR1 nucleic acid sequence may be inserted into a single vector such that a host organism transformed or transfected with said vector would produce multiple HVR1 proteins. For example, a polycistrionic vector in which multiple different HVR1 proteins may be expressed from a single vector is created by placing expression of each protein under control of an internal ribosomal entry site (IRES) (Molla, A. et al. *Nature*, 356:255–257 (1992); Gong, S. K. et al. *J. of Virol.*, 263:1651–1660 (1989)).

In another embodiment, restriction digest fragments containing a sequence coding for HVR1 proteins can be inserted into a suitable expression vector that functions in prokaryotic or eukaryotic cells. By suitable is meant that the vector is capable of carrying and expressing a complete nucleic acid sequence coding for an HVR1 protein. Preferred expression vectors are those that function in a eukaryotic cell. Examples of such vectors include, but are not limited to, plasmid, vaccinia virus, adenovirus, retrovirus or herpes virus vectors.

In yet another embodiment, the selected recombinant expression vector may then be transfected into a suitable eukaryotic cell system for purposes of expressing the recombinant protein. Such eukaryotic cell systems include but are not limited to cell lines such as HeLa, MRC-5 or CV-1 or other monkey kidney cell substrates.

The expressed recombinant protein may be detected by methods known in the art including, but not limited to, Coomassie blue staining and Western blotting.

The present invention also relates to substantially purified and isolated recombinant HVR1 proteins. In one embodiment, the expressed recombinant protein can be obtained as a crude lysate or it can be purified by standard protein purification procedures known in the art which may include differential precipitation, molecular sieve chromatography, ion-exchange chromatography, isoelectric focusing, gel electrophoresis and affinity and immunoaffinity chromatography. The recombinant protein may be purified by passage through a column containing a resin which has bound thereto antibodies specific for HVR1 protein.

Alternatively, those of ordinary skill in the art would be aware that the proteins of the present invention or analogs thereof can be synthesized by automated instruments sold by a variety of manufacturers or can be commercially custom-ordered and prepared. The term analog has been described earlier in the specification and for purposes of describing the proteins of the present invention, analogs can further include branched, cyclic or other non-linear arrangements of the amino acid sequences of the present invention.

The present invention therefore relates to the use of recombinant or synthetic HVR1 proteins as diagnostic agents and vaccines. In one embodiment, the proteins of this invention can be used in immunoassays for diagnosing or prognosing hepatitis C in a mammal. For the purposes of the present invention, "mammal" as used throughout the specification and claims, includes, but is not limited to humans, chimpanzees, other primates and the like. In a preferred embodiment, the immunoassay is useful in diagnosing hepatitis C infection in humans.

Immunoassays of the present invention may be those commonly used by those skilled in the art including, but not limited to, radioimmunoassay, Western blot assay, immunofluorescent assay, enzyme immunoassay, chemiluminescent assay, immunohistochemical assay, immunoprecipitation and the like. Standard techniques known in the art for ELISA are described in *Methods in Immunodiagnosis*, 2nd Edition, Rose and Bigazzi, eds., John Wiley and Sons, 1980 and Campbell et al., *Methods of Immunology*, W. A. Benjamin, Inc., 1964, both of which are incorporated herein by reference. Such assays may be a direct, indirect, competitive, or noncompetitive immunoassay as described in the art (Oellerich, M. 1984. *J. Clin. Chem. Clin.* BioChem 22:895–904) Biological samples appropriate for such detection assays include, but are not limited to serum, liver, saliva, lymphocytes or other mononuclear cells.

In a preferred embodiment, test serum is reacted with a solid phase reagent having surface-bound recombinant HVR1 protein(s) as antigen(s). The solid surface reagent can be prepared by known techniques for attaching protein to solid support material. These attachment methods include non-specific adsorption of the protein to the support or covalent attachment of the protein to a reactive group on the support. After reaction of the antigen with anti-HCV antibody, unbound serum components are removed by washing and the antigen-antibody complex is reacted with a secondary antibody such as labelled anti-human antibody. The label may be an enzyme which is detected by incubating the solid support in the presence of a suitable fluorimetric or calorimetric reagent. Other detectable labels may also be used, such as radiolabels or colloidal gold, and the like.

The HCV HVR1 proteins and analogs thereof may be prepared in the form of a kit, alone, or in combinations with other reagents such as secondary antibodies, for use in immunoassays. It is understood by those of ordinary skill in the art that due to the variability between HVR1 amino acid sequences between genotypes, the use of a single HVR1 protein as an antigen in the above-described immunoassays may be useful in detecting a single genotype of HCV. Alternatively, the use of HVR1 proteins of multiple genotypes as antigens in the above-described immunoassays can serve as universal probes capable of detecting all genotypes of HCV.

In yet another embodiment, the HVR1 proteins or analogs thereof can be used as a vaccine to protect mammals against challenge with hepatitis C. The vaccine, which acts as an immunogen, may be a cell, cell lysate from cells transfected with a recombinant expression vector or a culture supernatant containing the expressed protein. Alternatively, the immunogen is a partially or substantially purified recombinant protein or a chemically synthesized protein. In a preferred embodiment, HVR1 proteins having amino acid sequences found in multiple HCV isolates from different genotypes are administered together to provide protection against challenge with multiple isolates of HCV or a synthetic protein.

While it is possible for the immunogen to be administered in a pure or substantially pure form, it is preferable to present it as a pharmaceutical composition, formulation or preparation.

The formulations of the present invention, both for veterinary and for human use, comprise an immunogen as described above, together with one or more pharmaceutically acceptable carriers and optionally other therapeutic ingredients. The carrier(s) must be "acceptable" in the sense of being compatible with the other ingredients of the formulation and not deleterious to the recipient thereof. The formulations may conveniently be presented in unit dosage form and may be prepared by any method well-known in the pharmaceutical art.

All methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product into the desired formulation.

Formulations suitable for intravenous intramuscular, subcutaneous, or intraperitoneal administration conveniently comprise sterile aqueous solutions of the active ingredient with solutions which are preferably isotonic with the blood of the recipient. Such formulations may be conveniently prepared by dissolving the solid active ingredient in water containing physiologically compatible substances such as sodium chloride (e.g. 0.1–2.0 M), glycine, and the like, and having a buffered pH compatible with physiological conditions to produce an aqueous solution, and rendering said solution sterile. These may be present in unit or multi-dose containers, for example, sealed ampules or vials.

The formulations of the present invention may incorporate a stabilizer. Illustrative stabilizers are preferably incorporated in an amount of 0.10–10,000 parts by weight per part by weight of immunogens. If two or more stabilizers are to be used, their total amount is preferably within the range specified above. These stabilizers are used in aqueous solutions at the appropriate concentration and pH. The specific osmotic pressure of such aqueous solutions is generally in the range of 0.1–3.0 osmoles, preferably in the range of 0.8–1.2. The pH of the aqueous solution is adjusted to be within the range of 5.0–9.0, preferably within the range of 6–8. In formulating the immunogen of the present invention, an anti-adsorption agent may be used.

Additional pharmaceutical methods may be employed to control the duration of action. Controlled release preparations may be achieved through the use of polymer to complex or adsorb the proteins or their derivatives. The controlled delivery may be exercised by selecting appropriate macromolecules (for example polyester, polyamino acids, polyvinyl pyrrolidone, ethylenevinylacetate, methylcellulose, carboxymethylcellulose, or protamine sulfate) and the concentration of macromolecules as well as the methods of incorporation in order to control release. Another possible method to control the duration of action by controlled-release preparations is to incorporate the proteins, protein analogs or their functional derivatives, into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatin-microcapsules and poly (methylmethacylate) microcapsules, respectively, or in colloidal drug delivery systems, for example, liposomes, albumin microspheres, microemulsions, nanoparticles, and nanocapsules or in macroemulsions.

When oral preparations are desired, the compositions may be combined with typical carriers, such as lactose, sucrose, starch, talc, magnesium stearate, crystalline cellulose, methyl cellulose, carboxymethyl cellulose, glycerin, sodium alginate or gum arabic among others.

Vaccination can be conducted by conventional methods. For example, the immunogen or immunogens can be used in a suitable diluent such as saline or water, or complete or incomplete adjuvants. Further, the immunogen(s) may or may not be bound to a carrier to make the protein(s) immunogenic. Examples of such carrier molecules include but are not limited to bovine serum albumin (BSA), keyhole limpet hemocyanin (KLH), tetanus toxoid, and the like. The immunogen(s) can be administered by any route appropriate for antibody production such as intravenous, intraperitoneal, intramuscular, subcutaneous, and the like. The immunogen (s) may be administered once or at periodic intervals until a significant titer of anti-HCV antibody is produced. The antibody may be detected in the serum using an immunoassay. Doses of HVR1 protein(s) effective to elicit a protective antibody response against HCV infection range from about 0.1 to about 100 μg with a more preferred range being about 2 to about 20 μg.

In yet another embodiment, the immunogen may be a nucleic acid sequence or sequence capable of directing host organism synthesis of HVR1 protein(s). Such nucleic acid sequence(s) may be inserted into a suitable expression vector by methods known to those skilled in the art. Expression vectors suitable for producing high efficiency gene transfer in vivo include retroviral, adenoviral and vaccinia viral vectors. Operational elements of such expression vectors are disclosed previously in the present specification and are known to one skilled in the art. Such expression vectors can be administered intravenously, intramuscularly, intradermally, subcutaneously, intraperitoneally or orally.

In an alternative embodiment, direct gene transfer may be accomplished via intramuscular injection of, for example, plasmid-based eukaryotic expression vectors containing a nucleic acid sequence capable of directing host organism synthesis of HVR1 protein(s). Such an approach has previously been utilized to produce the hepatitis B surface antigen in vivo and resulted in an antibody response to the surface antigen (Davis, H. L. et al. (1993) *Human Molecular Genetics*, 2:1847–1851; see also Davis et al. (1993) *Human Gene Therapy*, 4:151–159 and 733–740). In a preferred embodiment, HVR1 nucleic acid sequences of isolates from multiple genotypes of HCV are administered together to provide protection against challenge with multiple genotypes of HCV.

Doses of HVR1 protein(s) -encoding nucleic acid sequence effective to elicit a protective antibody response against HCV infection range from about 0.5 to about 5000 μg. A more preferred range being about 10 to about 1000 μg.

The HVR1 proteins and expression vectors containing a nucleic acid sequence capable of directing host organism synthesis of HVR1 protein(s) may be supplied in the form of a kit, alone, or in the form of a pharmaceutical composition as described above.

The nucleic acid sequences of the present invention or primers/probes derived therefrom can also be used to analyze the RNA of a mammal for the presence of specific hepatitis C virus isolates.

The RNA to be analyzed can be isolated from serum, liver, saliva, lymphocytes or other mononuclear cells as viral RNA, whole cell RNA or as poly(A)$^+$ RNA. Whole cell RNA can be isolated by methods known to those skilled in the art. Such methods include extraction of RNA by differential precipitation (Birnbiom, H. C. (1988) Nucleic Acids Res., 16:1487–1497), extraction of RNA by organic solvents (Chomczynski, P. et al. (1987) Anal. Biochem., 162:156–159) and extraction of RNA with strong denaturants (Chirgwin, J. M. et al. (1979) Biochemistry, 18:5294–5299). Poly(A)$^+$ RNA can be selected from whole cell RNA by affinity chromatography on oligo-d(T) columns (Aviv, H. et al. (1972) Proc. Natl. Acad. Sci., 69:1408–1412) or Poly(U) RNA can be selected by affinity chromatography on oligo-d(A) columns. A preferred method of isolating RNA is extraction of viral RNA by the guanidinium-phenol-chloroform method of Bukh et al. (1992a).

The methods for analyzing the RNA for the presence of HCV include, but are not limited to, Northern blotting (Alwine, J. C. et al. (1977) Proc. Natl. Acad. Sci., 74:5350–5354), dot and slot blot hybridization (Kafatos, F. C. et al. (1979) Nucleic Acids Res., 7:1541–1522), filter hybridization (Hollander, M. C. et al. (1990) Biotechniques; 9:174–179), RNase protection (Sambrook, J. et al. (1989) in "Molecular Cloning, A Laboratory Manual", Cold Spring Harbor Press, Plainview, N.Y.) and reverse-transcription polymerase chain reaction (RT-PCR) (Watson, J. D. et al. (1992) in "Recombinant DNA" Second Edition, W. H. Freeman and Company, New York).

A preferred method for analyzing the RNA is RT-PCR. In this method, the RNA can be reverse transcribed to first strand cDNA using a primer or primers derived from the nucleotide sequences shown in SEQ ID NOs:1–49 or sequences complementary to those. Once the cDNAs are synthesized, PCR amplification is carried out using pairs of primers designed to hybridize with sequences in the hypervariable region which are an appropriate distance apart (at least about 50 nucleotides) to permit amplification of the cDNA and subsequent detection of the amplification product. Each primer of a pair is a single-stranded oligonucleotide of about 15 to about 40 bases in length with a more preferred range being about 20 to about 30 bases in length where one primer (the "upstream" primer) is complementary to the original RNA and the second primer (the "downstream" primer) is complementary to the first strand of cDNA generated by reverse transcription of the RNA. Optimization of the amplification reaction to obtain sufficiently specific hybridization to the nucleotide sequence of interest is well within the skill in the art and is preferably achieved by adjusting the annealing temperature.

The amplification products of PCR can be detected either directly or indirectly. In one embodiment, direct detection of the amplification products is carried out via labelling of primer pairs. Labels suitable for labelling the primers of the present invention are known to one skilled in the art and include radioactive labels, biotin, avidin, enzymes and fluorescent molecules. The derived labels can be incorporated into the primers prior to performing the amplification reaction. A preferred labelling procedure utilizes radiolabeled ATP and T4 polynucleotide kinase (Sambrook, J. et al. (1989) in "Molecular Cloning, A Laboratory Manual", Cold Spring Harbor Press, Plainview, N.Y.). Alternatively, the desired label can be incorporated into the primer extension products during the amplification reaction in the form of one or more labelled dNTPs. In the present invention, the labelled amplified PCR products can be detected by agarose gel electrophoresis followed by ethidium bromide staining and visualization under ultraviolet light or via direct sequencing of the PCR-products.

In yet another embodiment, unlabelled amplification products can be detected via hybridization with labelled nucleic acid probes radioactively labelled or, labelled with biotin, in methods known to one skilled in the art such as dot and slot blot hybridization (Kafatos, F. C. et al. (1979) or filter hybridization (Hollander, M. C. et al. (1990)).

In one embodiment, the nucleic acid sequences used as probes are selected from, and substantially homologous to, SEQ ID NOs:1–49. In an alternative embodiment, the sequence alignments shown in FIGS. 1A–1K may be used to design hybridization probes.

The nucleic acid sequence used as a probe to detect PCR amplification products of the present invention can be labeled in single-stranded or double-stranded form. Labelling of the nucleic acid sequence can be carried out by techniques known to one skilled in the art. Such labelling techniques can include radiolabels and enzymes (Sambrook, J. et al. (1989) in "Molecular Cloning, A Laboratory Manual", Cold Spring Harbor Press, Plainview, N.Y.). In addition, there are known non-radioactive techniques for signal amplification including methods for attaching chemical moieties to pyrimidine and purine rings (Dale, R. N. K. et al. (1973) *Proc. Natl. Acad. Sci.*, 70:2238–2242; Heck, R. F. (1968) *S. Am. Chem. Soc.*, 90:5518–5523), methods which allow detection by chemiluminescence (Barton, S. K. et al. (1992) *J. Am. Chem. Soc.*, 114:8736–8740) and methods utilizing biotinylated nucleic acid probes (Johnson, T. K. et al. (1983) *Anal. Biochem.*, 133:126–131; Erickson, P. F. et al. (1982) *J. of Immunology Methods*, 51:241–249; Matthaei, F. S. et al. (1986) *Anal. Biochem.*, 157:123–128) and methods which allow detection by fluorescence using commercially available products.

The administration of the nucleic acid sequences or proteins of the present invention as immunogens may be for either a prophylactic or therapeutic purpose. When provided prophylactically, the immunogen(s) is provided in advance of any exposure to HCV or in advance of any symptom(s) due to HCV infection. The prophylactic administration of the immunogen serves to prevent or attenuate any subsequent infection of HCV in a mammal. When provided therapeutically, the immunogen(s) is provided at (or shortly after) the onset of the infection or at the onset of any symptom of infection or disease caused by HCV or at any time thereafter. The therapeutic administration of the immunogen(s) serves to attenuate or eradicate the infection or disease.

In addition to use as a vaccine, the compositions can be used to prepare antibodies to the HVR1 protein. The antibodies can be used directly as antiviral agents or they may be used in immunoassays disclosed herein to detect the presence of the Hepatitis C virus in patient sera. To prepare antibodies, a host animal can be immunized using the HVR1 proteins of the present invention or expression vectors containing nucleic acid sequences encoding such proteins. The host serum or plasma is collected following an appropriate time interval to provide a composition comprising antibodies reactive with the HVR1 region protein of the virus particle. The gamma globulin fraction or the IgG antibodies can be obtained, for example, by use of saturated ammonium sulfate or DEAE Sephadex, or other techniques known to those skilled in the art. The antibodies are substantially free of many of the adverse side effects which may be associated with other anti-viral agents such as drugs.

The antibody compositions can be made even more compatible with the host system by minimizing potential adverse immune system responses. This is accomplished by removing all or a portion of the Fc portion of a foreign species antibody or using an antibody of the same species as the host animal, for example, the use of antibodies from human/human hybridomas. Humanized antibodies (i.e., nonimmunogenic in a human) may be produced, for example, by replacing an immunogenic portion of an antibody with a corresponding, but nonimmunogenic portion (i.e., chimeric antibodies). Such chimeric antibodies may contain the reactive or antigen-binding portion of an antibody from one species and the Fc portion of an antibody (nonimmunogenic) from a different species. Examples of chimeric antibodies, include but are not limited to, non-human mammal-human chimeras, rodent-human chimeras, murine-human and rat-human chimeras (Robinson et al., International Patent Application 184,187; Taniguchi M., European Patent Application 171,496; Morrison et al., European Patent Application 173,494; Neuberger et al., PCT Application WO 86/01533; Cabilly et al., 1987 Proc. Natl. Acad. Sci. USA 84:3439; Nishimura et al., 1987 Canc. Res. 47:999; Wood et al., 1985 Nature 314:446; Shaw et al., 1988 J. Natl. Cancer Inst. 80:15553, all incorporated herein by reference).

General reviews of "humanized" chimeric antibodies are provided by Morrison S., 1985 Science 229:1202 and by Oi et al., 1986 BioTechniques 4:214.

Suitable "humanized" antibodies can be alternatively produced by CDR or CEA substitution (Jones et al., 1986 Nature 321:552; Verhoeyan et al., 1988 Science 239:1534; Biedleret al. 1988 J. Immunol. 141:4053, all incorporated herein by reference).

The antibodies or antigen binding fragments may also be produced by genetic engineering. The technology for expression of both heavy and light chain genes in *E. coli* is the subject of the PCT patent applications; publication number WO 901443, W0901443, and WO 9014424 and in Huse et al., 1989 Science 246:1275–1281.

The antibodies can also be used as a means of enhancing the immune response. The antibodies can be administered in amounts similar to those used for other therapeutic administrations of antibody. For example, normal immune globulin is administered at 0.02–0.1 ml/lb body weight during the early incubation period of other viral diseases such as rabies, measles, and hepatitis B to interfere with viral entry into cells. Thus, antibodies reactive with the HVR1 proteins can be passively administered alone or in conjunction with another antiviral agent to a host infected with an HCV to enhance the immune response and/or the effectiveness of an antiviral drug.

Alternatively, antibodies to the HVR1 region can be induced by administered anti-idiotype antibodies as immunogens. Conveniently, a purified antibody preparation prepared as described above is used to induce anti-idiotype antibody in a host animal, the composition is administered to the host animal in a suitable diluent. Following administration, usually repeated administration, the host produces anti-idiotype antibody. To eliminate an immunogenic response to the Fc region, antibodies produced by the same species as the host animal can be used or the Fc region of the administered antibodies can be removed. Following induction of anti-idiotype antibody in the host animal, serum or plasma is removed to provide an antibody composition. The composition can be purified as described above for anti-HVR1 antibodies, or by affinity chromatography using anti-HVR1 antibodies bound to the affinity matrix. The anti-idiotype antibodies produced or similar in conformation to the authentic HVR1 amino acid sequence may be used to prepare an HCV vaccine rather than using an HVR1 protein.

When used as a means of inducing anti-HCV virus antibodies in an animal, the manner of injecting the antibody is the same as for vaccination purposes, namely intramuscularly, intraperitoneally, subcutaneously or the like in an effective concentration in a physiologically suitable diluent with or without adjuvant. One or more booster injections may be desirable.

The HVR1 proteins of the invention are also intended for use in producing antiserum designed for pre- or post-exposure prophylaxis. Here an HVR1 protein, or mixture of HVR1 proteins is formulated with a suitable adjuvant and administered by injection to human volunteers, according to known methods for producing human antisera. Antibody response to the injected proteins is monitored, during a several-week period following immunization, by periodic serum sampling to detect the presence of anti-HVR1 serum antibodies, using an immunoassay as described herein.

The antiserum from immunized individuals may be administered as a pre-exposure prophylactic measure for individuals who are at risk of contracting infection. The antiserum is also useful in treating an individual post-exposure, analogous to the use of high titer antiserum against hepatitis B virus for post-exposure prophylaxis.

For both in vivo use of antibodies to HVR1 proteins and anti-idiotype antibodies and diagnostic use, it may be preferable to use monoclonal antibodies. Monoclonal anti-HVR1 protein antibodies or anti-idiotype antibodies can be produced as follows. The spleen or lymphocytes from an immunized animal are removed and immortalized or used to prepare hybridomas by methods known to those skilled in the art. (Goding, J. W. 1983. Monoclonal Antibodies: Principles and Practice, Pladermic Press, Inc., New York, N.Y., pp. 56–97). To produce a human—human hybridoma, a human lymphocyte donor is selected. A donor known to be infected with HCV (where infection has been shown for example by the presence of anti-virus antibodies in the blood or by virus culture) may serve as a suitable lymphocyte donor. Lymphocytes can be isolated from a peripheral blood sample or spleen cells may be used if the donor is subject to splenectomy. Epstein-Barr virus (EBV) can be used to immortalize human lymphocytes or a human fusion partner can be used to produce human—human hybridomas. Primary in vitro immunization with peptides can also be used in the generation of human monoclonal antibodies.

Antibodies secreted by the immortalized cells are screened to determine the clones that secrete antibodies of the desired specificity. For monoclonal antibodies to the HVR1 amino acid sequences disclosed herein, the antibodies must bind to HVR1 proteins. For monoclonal anti-idiotype antibodies, the antibodies must bind to anti-HVR1 protein antibodies. Cells producing antibodies of the desired specificity are selected.

The present invention also relates to the use of single-stranded antisense poly- or oligonucleotides derived from nucleotide sequences substantially homologous to those shown in SEQ ID NOs:1–49 to inhibit the expression of hepatitis C E2 genes. By substantially homologous as used throughout the specification and claims to describe the nucleic acid sequences of the present invention, is meant a level of homology between the nucleic acid sequence and the SEQ ID NOs. referred to in the above sentence. Preferably, the level of homology is in excess of 80%, more preferably in excess of 90%, with a preferred nucleic acid sequence being in excess of 95% homologous with the DNA sequence shown in the indicated SEQ ID NO. These antisense poly- or oligonucleotides can be either DNA or RNA. The targeted sequence is typically messenger RNA and more preferably, a single sequence required for processing or translation of the RNA. The anti-sense poly- or oligonucleotides can be conjugated to a polycation such as polylysine as disclosed in Lemaitre, M. et al. ((1989) *Proc. Natl. Acad. Sci. USA*, 84:648–652) and this conjugate can be administrated to a mammal in an amount sufficient to hybridize to and inhibit the function of the messenger RNA.

Any articles or patents referenced herein are incorporated by reference. The following examples illustrate various aspects of the invention but are in no way intended to limit the scope thereof.

EXAMPLE 1

Use Of HVR1 Protein Or Nucleic Acid Sequence Encoding HVR1 Protein As A Vaccine Mammals are immunized intradermally or intramuscularly with 2 to 20 μg of at least one HVR1 protein having an amino acid sequence of at least six contiguous amino acids selected from the amino acid sequence shown in SEQ ID NOs:50–98 or with 10 to 1000 μg of expression vector containing at least one nucleic acid having a sequence of at least 15 nucleotides selected from SEQ ID NOs:1–49 to stimulate production of protective antibodies. Those of ordinary skill in the art would readily understand that the HVR1 protein or the expression vector containing HVR1 nucleic acid sequence can be used alone or in combination with other HVR1 proteins or other expression vectors containing different HVR1 nucleic acid sequences presented herein. When HVR1 proteins or nucleic acid sequences from multiple isolates are used as immunogens, the immunized mammals are protected from challenge with multiple isolates of HCV.

EXAMPLE 2

Use Of Antisera To The HVR1 Protein Sequences In Pre- or Post-Exposure Prophylaxis Antisera collected from a mammal injected with a protein having an amino acid sequence of at least six contiguous amino acids selected from the amino acid sequences shown in SEQ ID NOS 50–98 or, a mixture of such proteins, is administered intravenously to an individual post-exposure to HCV or is administered to an uninfected mammal in an amount effective to protect against hepatitis C infection. Such administration is repeated one or more times at monthly intervals and serves to reduce the severity of the HCV infection as indicated by, for example, diminished replication of HCV.

We claim:

1. A purified and isolated protein having an amino acid sequence selected from the group consisting of SEQ ID NO:50 through SEQ ID NO:98.

2. A method of preventing hepatitis C, comprising administering the composition of claim 1 to a mammal in an amount effective to stimulate the production of protective antibody.

3. A vaccine for immunizing a mammal against hepatitis C comprising at least one protein according to claim 1 in a pharmacologically acceptable carrier.

4. A protein produced by a host organism transformed or transfected with a recombinant expression vector comprising a nucleic acid sequence which encodes an amino acid sequence selected from the group consisting of SEQ ID NO:50 through SEQ ID NO:98.

5. A vaccine for immunizing a mammal against hepatitis C comprising at least one protein according to claim 4.

6. A composition comprising at least one protein of claim 1 and an excipient, diluent or carrier.

7. A purified and isolated amino acid molecule having a sequence consisting of from six to thirty two amino acids, where said sequence is a contiguous sequence found in a sequence selected from the group consisting of SEQ ID NO:50 through SEQ ID NO:57 and SEQ ID NO:60 through SEQ ID NO:98.

8. A composition comprising at least one molecule of claim 7 and an excipient, diluent or carrier.

9. A method of preventing hepatitis C, said method comprising administering the composition of claim 8 to a mammal in an amount effective to stimulate the production of protective antibody.

10. A vaccine for immunizing a mammal against hepatitis C, said vaccine comprising at least one molecule of claim 7 in a pharmacologically acceptable carrier.

11. A protein produced by a host organism transformed or transfected with a recombinant expression vector comprising a nucleic acid sequence which encodes an amino acid sequence consisting of from six to thirty two amino acids, where said sequence is a contiguous sequence found in a sequence selected from the group consisting of SEQ ID NO:50 through SEQ ID NO:57 and SEQ ID NO:60 through SEQ ID NO:98.

12. A purified and isolated amino acid molecule having a sequence consisting of from six to thirty two amino acids, where said sequence is a contiguous sequence found in a sequence selected from the group consisting of SEQ ID NO:58 and SEQ ID NO:59.

13. A composition comprising at least one molecule of claim 12 and an excipient, diluent or carrier.

14. A method of preventing hepatitis C, said method comprising administering the composition of claim 13 to a mammal in an amount effective to stimulate the production of protective antibody.

15. A vaccine for immunizing a mammal against hepatitis C, said vaccine comprising at least one molecule of claim 12 in a pharmacologically acceptable carrier.

16. A protein produced by a host organism transformed or transfected with a recombinant expression vector comprising a nucleic acid sequence which encodes an amino acid sequence consisting of from six to thirty two amino acids, where said sequence is a contiguous sequence found in a sequence selected from the group consisting of SEQ ID NO:50 through SEQ ID NO:98.

* * * * *

SEQUENCE LISTING

```
(1) GENERAL INFORMATION:

   (iii) NUMBER OF SEQUENCES:  98


(2) INFORMATION FOR SEQ ID NO:1:

     (i) SEQUENCE CHARACTERISTICS:
          (A) LENGTH:  96 base pairs
          (B) TYPE:  nucleic acid
          (C) STRANDEDNESS:  single
          (D) TOPOLOGY:  linear
```

-continued (vi) ORIGINAL SOURCE:
(A) ORGANISM: homosapiens
(C) INDIVIDUAL ISOLATE: S18

(xi) SEQUENCE DESCRIPTION: SEQ ID NO:1:

GAC ACC TAC GCC ACT GGG GGG AGT GCC AGC AGG ACC ACG 39

CAG GCG TTC ACT AGG TTC TTC TCT CCG GGC GCC AAG CAG 78

GAC ATC CAG CTA ATC AAC 96

(2) INFORMATION FOR SEQ ID NO:2:

(i) SEQUENCE CHARACTERISTICS:
(A) LENGTH: 96 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: S14

(xi) SEQUENCE DESCRIPTION: SEQ ID NO:2:

GAC ACC TAC ATC ACC GGG GGA ACT GCC GGT CGC ACC GTG 39

GGG ACA CTC AGC AAT CTC CTC GCA CCG GGC GCC AAG CAG 78

AAC ATC CAG CTG ATT AAC 96

(2) INFORMATION FOR SEQ ID NO:3:

(i) SEQUENCE CHARACTERISTICS:
(A) LENGTH: 96 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: DK7

(xi) SEQUENCE DESCRIPTION: SEQ ID NO:3:

AGC ACC CAC GTC ACC GGG GGA ACT GCC GCC CGC GCT GCG 39

TTT GGC ATT ACT AGT CTC TTT GCA CCA GGC GCC AAA CAG 78

AAC ATC CAA CTG ATC AGC 96

(2) INFORMATION FOR SEQ ID NO:4:

(i) SEQUENCE CHARACTERISTICS:
(A) LENGTH: 96 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: US11

(xi) SEQUENCE DESCRIPTION: SEQ ID NO:4:

GAA ACC TAC GTC ACC GGG GGA AGT GCC GGC CAT GCC GCG 39

TCT GGA CTT GCT GGT CTT TTC TCA CAA GGC GCC CAG CAG 78

AAC ATC CAG CTG ATC AAC 96

(2) INFORMATION FOR SEQ ID NO:5:

-continued (i) SEQUENCE CHARACTERISTICS:
(A) LENGTH: 96 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: SW1

(xi) SEQUENCE DESCRIPTION: SEQ ID NO:5:

GAA ACC TAC ACC ACC GGG GGG GCT GCT GGT CAG ACC GCG 39

TCT GGA TTC ACC AGT CTT TTC ACG CGG GGC GCC CAG CAG 78

AAT ATC CAG CTG GTC AAC 96

(2) INFORMATION FOR SEQ ID NO:6:

(i) SEQUENCE CHARACTERISTICS:
(A) LENGTH: 96 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: DK9

(xi) SEQUENCE DESCRIPTION: SEQ ID NO:6:

GAC ACC CGC GTC ACC GGG GGG AGC GCT GCC AGG AAC ACG 39

TAT GGA CTC GCC AGT CTT CTC AGC CCG GGC GCC AAG CAG 78

AAT ATT CAG CTG ATC AAC 96

(2) INFORMATION FOR SEQ ID NO:7:

(i) SEQUENCE CHARACTERISTICS:
(A) LENGTH: 96 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: DR4

(xi) SEQUENCE DESCRIPTION: SEQ ID NO:7:

GGC ACC CAA GTC AGC GGG GGG AGC GCC GCT CGC ACC GTG 39

AAT GCA CTC GCT GGT CTC TTC GAC CAG GGC GCG CGG CAG 78

AAT ATC CAG TTG ATC AAC 96

(2) INFORMATION FOR SEQ ID NO:8:

(i) SEQUENCE CHARACTERISTICS:
(A) LENGTH: 96 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: DR1

(xi) SEQUENCE DESCRIPTION: SEQ ID NO:8:

ACC ACC CAT GTC ACT GGG GGA AGT GAA GCT CGC GCC GCG 39

TCT GCA CTC ACT GGT CTC TTC ACG CGG GGC GCG CGG CAG 78

-continued

AAC GTC CAG TTG ATC AAC 96

(2) INFORMATION FOR SEQ ID NO:9:

(i) SEQUENCE CHARACTERISTICS:
(A) LENGTH: 108 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: D3

(xi) SEQUENCE DESCRIPTION: SEQ ID NO:9:

CGT GGA GGC GTG GGC ACC CAC ACG ATA GGG GGG GCG CAA 39

GCC TAC AGC GTT AGG GGG TTC ACG TCC ATA TTT TCA ACT 78

GGG CCG GCT CAG AAG ATC CAG CTT GTA AAC 108

(2) INFORMATION FOR SEQ ID NO:10:

(i) SEQUENCE CHARACTERISTICS:
(A) LENGTH: 108 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: D1

(xi) SEQUENCE DESCRIPTION: SEQ ID NO:10:

AGT GCA TCC CCG GGC ACC CGC ACG ATA GGG GGG TCG CAA 39

GCC AAA CAC ACT AGC AGT ATC GTG TCC ATG TTC TCA CTT 78

GGG CCG TCT CAG AAA ATC CAG CTT GTA AAC 108

(2) INFORMATION FOR SEQ ID NO:11:

(i) SEQUENCE CHARACTERISTICS:
(A) LENGTH: 96 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: P10

(xi) SEQUENCE DESCRIPTION: SEQ ID NO:11:

CGC ACC CAC ACG ACG GGG GGG TCG GTG GCC TAC GGC ACC 39

CGC AGG TTT ACG TCC CTC TTT ACA TCT GGG GCG TCT CAG 78

AAA ATC CAG CTT GTG AAC 96

(2) INFORMATION FOR SEQ ID NO:12:

(i) SEQUENCE CHARACTERISTICS:
(A) LENGTH: 96 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: T10

(xi) SEQUENCE DESCRIPTION: SEQ ID NO:12:

-continued

AGC ACC CGC GTA ACA GGG GGA ACG GCA GCC CGC AAC ACC 39

TAC GGG CTC GCG TCC ATC TTT GCA CCT GGG GCG TCT CAG 78

AAG ATC CAG CTT ATA AAC 96

(2) INFORMATION FOR SEQ ID NO:13:

(i) SEQUENCE CHARACTERISTICS:
(A) LENGTH: 96 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: HK5

(xi) SEQUENCE DESCRIPTION: SEQ ID NO:13:

GCC ACC CAC GTG ACA GGG GGT ACT GCA GCC CAC ACC ACT 39

CGT GGG CTC ACG TCC CTG TTC GCC CCT GGG CCT TCT CAG 78

AAA ATC CAG CTT ATA AAT 96

(2) INFORMATION FOR SEQ ID NO:14:

(i) SEQUENCE CHARACTERISTICS:
(A) LENGTH: 96 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: HK8

(xi) SEQUENCE DESCRIPTION: SEQ ID NO:14:

GAT ACC TAC GTG TCA GGG GGT GCG ACA GCC CGC AAC ACT 39

TAC GGG CTT ACG TCC CTC TTC ACC CCA GGG GCT GCT CAG 78

AAA ATC CAG CTT ATA AAC 96

(2) INFORMATION FOR SEQ ID NO:15:

(i) SEQUENCE CHARACTERISTICS:
(A) LENGTH: 96 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: T3

(xi) SEQUENCE DESCRIPTION: SEQ ID NO:15:

ACA ACC CAC GTG TCA GGG GGG GTG TCG GCT CGC ACC ACC 39

CAC GGG CTG GCA TCC TTC TTT TCA CCT GGG CCG TCT CAG 78

AAA ATC CAG CTC GTA AAC 96

(2) INFORMATION FOR SEQ ID NO:16:

(i) SEQUENCE CHARACTERISTICS:
(A) LENGTH: 96 base pairs
(B) TYPE: nucleic acid
(C) STRANDEDNESS: single
(D) TOPOLOGY: linear -continued (vi) ORIGINAL SOURCE:
(A) ORGANISM: homosapiens
(C) INDIVIDUAL ISOLATE: SW2

(xi) SEQUENCE DESCRIPTION: SEQ ID NO:16:

AAC ACC TAC ACG ACA GGG GGA GAG GCA GCC TAC AAT ACC 39

CGC GGC TTT GCG AGT ATC TTC TCA AGC GGG CCG TCT CAG 78

AAA ATC CAG CTC GTA AAC 96

(2) INFORMATION FOR SEQ ID NO:17:

(i) SEQUENCE CHARACTERISTICS:
(A) LENGTH: 96 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: SA10

(xi) SEQUENCE DESCRIPTION: SEQ ID NO:17:

GGG ACC TAC ACG ACA GGG GGG GCG CAA GGC CGC ACC ACC 39

TCC AGC TTC GTG GGT CTC TTC ACC CCT GGG CCG TCT CAG 78

AGA ATC CAG CTC GTA AAC 96

(2) INFORMATION FOR SEQ ID NO:18:

(i) SEQUENCE CHARACTERISTICS:
(A) LENGTH: 96 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: US6

(xi) SEQUENCE DESCRIPTION: SEQ ID NO:18:

GAG ACT CAC GTG ACG GGG GGG GCG CAA GCC TAC GCC GCC 39

CGC AGT TTC ACG TCT CTC TTC ACA CCT GGG TCA CGT CAG 78

AAT ATC CAG CTT ATA AAC 96

(2) INFORMATION FOR SEQ ID NO:19:

(i) SEQUENCE CHARACTERISTICS:
(A) LENGTH: 96 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: IND5

(xi) SEQUENCE DESCRIPTION: SEQ ID NO:19:

CAG GCC AAG ACA ATA GGG GGG CGC CAA GCC CAC ACC ACC 39

GGG CGC CTT GTG TCT ATG TTC ACC CCT GGG CCG TCC CAG 78

AAC ATC CAG CTT GTA AAC 96

(2) INFORMATION FOR SEQ ID NO:20:

(i) SEQUENCE CHARACTERISTICS:

-continued (A) LENGTH: 96 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: IND8

(xi) SEQUENCE DESCRIPTION: SEQ ID NO:20:

CAC ACC AAC ATA ATA GGG GGG AGG GAA GCC TCC ACC ACC 39

CAA GGC TTT ACG AGT CTT TTC AGC CCT GGA GCG TCC CAG 78

AAA ATC CAG CTT GTA AAC 96

(2) INFORMATION FOR SEQ ID NO:21:

(i) SEQUENCE CHARACTERISTICS:
(A) LENGTH: 96 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: HK3

(xi) SEQUENCE DESCRIPTION: SEQ ID NO:21:

AGC ACC CAC ACG ATA GGG GCA ACT GTG GCC CGC ACC ACT 39

CAG AGT TGG ACG GGC TTC TTC AGC TCC GGG CCC TCT CAG 78

AAA ATC CAG CTT ATA AAT 96

(2) INFORMATION FOR SEQ ID NO:22:

(i) SEQUENCE CHARACTERISTICS:
(A) LENGTH: 96 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: S9

(xi) SEQUENCE DESCRIPTION: SEQ ID NO:22:

GGC ACC ACC GTG ACG GGA GCG GTG CAA GGC CGT TCC CTC 39

CAA GGG CTC ACT GGC CTT TTT TCC TCT GGA CCG ACT CAG 78

AAA CTC CAG CTT GTA AAT 96

(2) INFORMATION FOR SEQ ID NO:23:

(i) SEQUENCE CHARACTERISTICS:
(A) LENGTH: 96 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: HK4

(xi) SEQUENCE DESCRIPTION: SEQ ID NO:23:

AAC ACC TAC GTG ACA GGG GGG GCG GCA AGC CAT TCC ACC 39

CGA GGG CTC ACG TCC CTT TTC ACA ACG GGG GCG TCT CAG 78

AAA ATC CAG CTT ATA AAC 96

-continued (2) INFORMATION FOR SEQ ID NO:24:

(i) SEQUENCE CHARACTERISTICS:
(A) LENGTH: 96 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: S45

(xi) SEQUENCE DESCRIPTION: SEQ ID NO:24:

GGT ACC TAC ACG TCG GGG CAG GCG GCG GGC CGC ACC ACC 39

GCC GGG TTT ACG TCC ATC TTT AAC CCT GGG TCG GCT CAG 78

AGC ATC CAG CTC ATA AAC 96

(2) INFORMATION FOR SEQ ID NO:25:

(i) SEQUENCE CHARACTERISTICS:
(A) LENGTH: 96 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: DK1

(xi) SEQUENCE DESCRIPTION: SEQ ID NO:25:

ACC ACC CAC GTG ACG GGG GCG GTG CAG GGC CGC ACC ACC 39

CAA GGT TTC GCG TCC CTC TTC TCA CCC GGA TCG GCC CAG 78

AAA ATC CAG CTT GTA AAC 96

(2) INFORMATION FOR SEQ ID NO:26:

(i) SEQUENCE CHARACTERISTICS:
(A) LENGTH: 96 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: US10

(xi) SEQUENCE DESCRIPTION: SEQ ID NO:26:

GCA ACC AGG ACG GTT GGG CAT TCT GCA GCG TAC ACC GCC 39

TCC ACT TTC GCC GGC ATC TTC AAC GCT GGC TCT AGG CAG 78

AAC ATC CAG CTC ATC AAC 96

(2) INFORMATION FOR SEQ ID NO:27:

(i) SEQUENCE CHARACTERISTICS:
(A) LENGTH: 96 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: T4

(xi) SEQUENCE DESCRIPTION: SEQ ID NO:27:

-continued

```
AGC TCC ACC ACC ATT GGG AGT GCT GTC GCG AGC ACC ACC                    39

AGA GGC CTC ACC GGC TTG TTC TCC CCA GGC TCT CAG CAG                    78

AAC ATC CAG CTC ATT AAC                                                96


(2) INFORMATION FOR SEQ ID NO:28:

     (i) SEQUENCE CHARACTERISTICS:
          (A) LENGTH:  96 base pairs
          (B) TYPE:  nucleic acid
          (C) STRANDEDNESS:  single
          (D) TOPOLOGY:  linear

    (vi) ORIGINAL SOURCE:
          (A) ORGANISM:  homosapiens
          (C) INDIVIDUAL ISOLATE:  T9

    (xi) SEQUENCE DESCRIPTION: SEQ ID NO:28:

ACC ACC CAT ACA TCT GGG GGC ACC GCC GGG CAT ACA GCC                    39

TAT GGC CTC ACC AGC ATC TTC AGC CCT GGC GCC CGG CAG                    78

AAA ATC CAG CTC ATT TAT                                                96


(2) INFORMATION FOR SEQ ID NO:29:

     (i) SEQUENCE CHARACTERISTICS:
          (A) LENGTH:  96 base pairs
          (B) TYPE:  nucleic acid
          (C) STRANDEDNESS:  single
          (D) TOPOLOGY:  linear

    (vi) ORIGINAL SOURCE:
          (A) ORGANISM:  homosapiens
          (C) INDIVIDUAL ISOLATE:  T2

    (xi) SEQUENCE DESCRIPTION: SEQ ID NO:29:

CAC ACC GAG CTC ACC GGG AGT AAT GCC GGG CGT ACC ACC                    39

CAG GGC CTC GCT GCC TTC TTC ACC CCT GGC GCT AGC CAG                    78

AGG GTT CAG CTC ATT AAC                                                96


(2) INFORMATION FOR SEQ ID NO:30:

     (i) SEQUENCE CHARACTERISTICS:
          (A) LENGTH:  96 base pairs
          (B) TYPE:  nucleic acid
          (C) STRANDEDNESS:  single
          (D) TOPOLOGY:  linear

    (vi) ORIGINAL SOURCE:
          (A) ORGANISM:  homosapiens
          (C) INDIVIDUAL ISOLATE:  T8

    (xi) SEQUENCE DESCRIPTION: SEQ ID NO:30:

ACC ACC TAT ACT ACC GGC GCA CAA GTG GCT CGT ACC ACT                    39

GCT AGT CTT GCC GGC CTC TTC ACC ACC GGT CCT CAG CAG                    78

AAA ATC AAC TTA ATC AAT                                                96


(2) INFORMATION FOR SEQ ID NO:31:

     (i) SEQUENCE CHARACTERISTICS:
          (A) LENGTH:  96 base pairs
          (B) TYPE:  nucleic acid
          (C) STRANDEDNESS:  single
          (D) TOPOLOGY:  linear

    (vi) ORIGINAL SOURCE:
```

-continued (A) ORGANISM: homosapiens
(C) INDIVIDUAL ISOLATE: DK8

(xi) SEQUENCE DESCRIPTION: SEQ ID NO:31:

GCC ACT TAT ACC ACC GGC GGA CAA GCG GCT AGG GAC ACC 39

TGG GGG CTT GCT CGC CTC TTC TCC CCT GGC GCC CAG CAG 78

AAA CTC AGT TTG ATC AAC 96

(2) INFORMATION FOR SEQ ID NO:32:

(i) SEQUENCE CHARACTERISTICS:
(A) LENGTH: 96 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: DK11

(xi) SEQUENCE DESCRIPTION: SEQ ID NO:32:

AAC ACC CGT GTC ACC GGC GCG ATC GCG GGT CGG ACC GCC 39

GCA TCG CTT GCT AGC CTC TTT AAC TCT GGC CCC CAG CAG 78

AAA ATC AAT TTG ATC AAC 96

(2) INFORMATION FOR SEQ ID NO:33:

(i) SEQUENCE CHARACTERISTICS:
(A) LENGTH: 96 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: S83

(xi) SEQUENCE DESCRIPTION: SEQ ID NO:33:

ACC ACT TAT ACC ACT GGA GCA TCT GCT GGA CAG CAG GTA 39

CAG AGC TTC GCC AGA CTC TTC AGT CCG GGG CCC AAC CAG 78

CAT GTC CAG CTC GTC CGC 96

(2) INFORMATION FOR SEQ ID NO:34:

(i) SEQUENCE CHARACTERISTICS:
(A) LENGTH: 96 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: HK10

(xi) SEQUENCE DESCRIPTION: SEQ ID NO:34:

GGG ACA TAT ATC AGT GGT GGC CAC GTG GCT CGT GGT GCC 39

TCG GGG CTC GCC AGC TTT TTT TCT CCG GGC GCC AAA CAG 78

AAC CTG CAG CTG ATC AAT 96

(2) INFORMATION FOR SEQ ID NO:35:

(i) SEQUENCE CHARACTERISTICS:
(A) LENGTH: 96 base pairs

-continued (B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: S2

(xi) SEQUENCE DESCRIPTION: SEQ ID NO:35:

GAA ACA TAT GTC ACC GGT GGC AGT GCA GCT CGT AGT GCT 39

AGT AGG CTA GCT AGC TTC TTT TCT CCG GGC GCC CAG CAG 78

AAA CTG CAG CTG GTT AAC 96

(2) INFORMATION FOR SEQ ID NO:36:

(i) SEQUENCE CHARACTERISTICS:
(A) LENGTH: 96 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: S52

(xi) SEQUENCE DESCRIPTION: SEQ ID NO:36:

GAA ACA TAT GTC ACC GGT GGC AGT GTA GCT CAT AGT GCT 39

AGA GGG TTA ACT AGC CTT TTT AGT ATG GGC GCC AAG CAG 78

AAA CTG CAG TTG GTC AAC 96

(2) INFORMATION FOR SEQ ID NO:37:

(i) SEQUENCE CHARACTERISTICS:
(A) LENGTH: 96 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: S54

(xi) SEQUENCE DESCRIPTION: SEQ ID NO:37:

GCA ACA TAT ACC ACC GGT GGC AGT GCA GCT CAT AGT GCC 39

CAA GGG ATA ACT CGC CTT TTT AGT GTG GGC GCC AAA CAG 78

AAC CTG CAG TTG GTC AAC 96

(2) INFORMATION FOR SEQ ID NO:38:

(i) SEQUENCE CHARACTERISTICS:
(A) LENGTH: 96 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: DK12

(xi) SEQUENCE DESCRIPTION: SEQ ID NO:38:

ACC ACA CAC GTC ACC GGT GGC GAT GCA GCT CGT AGT ACC 39

CTC AGG TTT ACT AGC CTT TTT AGT GTG GGC TCC AAC CAG 78

CAA CTG CAG CTA GTC AAC 96

-continued (2) INFORMATION FOR SEQ ID NO:39:

(i) SEQUENCE CHARACTERISTICS:
(A) LENGTH: 96 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: Z4

(xi) SEQUENCE DESCRIPTION: SEQ ID NO:39:

CAC ACA TCT GTC AGC GGG GGC ACT CAG GCC CGA GCA GCC 39

CAA GGG TTG ACC AGC CTC TTT ACA TCT GGG CCC AGA CAA 78

AAC CTC CAG CTG ATA AAT 96

(2) INFORMATION FOR SEQ ID NO:40:

(i) SEQUENCE CHARACTERISTICS:
(A) LENGTH: 96 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: Z1

(xi) SEQUENCE DESCRIPTION: SEQ ID NO:40:

ACC ACG TAC GCT TCT GGC GCT GCG GCC GGC CGA ACC ACC 39

TCT GGC TTT GCC GGC CTA TTT ACC CCT GGC GCC AAG CAG 78

AAC ATC CGG CTT ATC AAC 96

(2) INFORMATION FOR SEQ ID NO:41:

(i) SEQUENCE CHARACTERISTICS:
(A) LENGTH: 96 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: Z7

(xi) SEQUENCE DESCRIPTION: SEQ ID NO:41:

ACG ACC ATG ACA ACC GGG GGA GCT GCT GCC CGC ACT GCC 39

CAC GCC TTC ACC GGC CTT TTC ACT TCT GGG CCC CAG CAA 78

AAA TTA CAG CTC ATT AAC 96

(2) INFORMATION FOR SEQ ID NO:42:

(i) SEQUENCE CHARACTERISTICS:
(A) LENGTH: 96 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: Z6

(xi) SEQUENCE DESCRIPTION: SEQ ID NO:42:

GAG ACC GTG ACA ACT GGG GGA AGC GTT GCT CGC AGC ACC 39

-continued

CGG GCC ATT ACT AGC CTC TTC AAT TCT GGG CCT AAG CAG 78

AAC CTA CAG CTC ATT AAT 96

(2) INFORMATION FOR SEQ ID NO:43:

(i) SEQUENCE CHARACTERISTICS:
(A) LENGTH: 96 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: DK13

(xi) SEQUENCE DESCRIPTION: SEQ ID NO:43:

GGC ACC TAC GTC ACC GGG GGC CAG GCG GGA CAG ACC GCG 39

TTT CAC CTT ACC GGA CTG TTC ACC AGG GGT TCC CAC CAG 78

AAC ATA CAG CTC ATT AAC 96

(2) INFORMATION FOR SEQ ID NO:44:

(i) SEQUENCE CHARACTERISTICS:
(A) LENGTH: 96 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: SA6

(xi) SEQUENCE DESCRIPTION: SEQ ID NO:44:

AGC ACC CAC AGT GTG GGG GGC TCT GCA GCT CAT ACT ACG 39

AGC GGC TTT ACC TCA CTT TTC AAC CCC GGG CCG AAG CAG 78

AAC TTG CAG CTC ATA TAC 96

(2) INFORMATION FOR SEQ ID NO:45:

(i) SEQUENCE CHARACTERISTICS:
(A) LENGTH: 96 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: SA1

(xi) SEQUENCE DESCRIPTION: SEQ ID NO:45:

CGC ACC CAC ACC GTG GCC GGT ACC GCT GCT TAC AGT ACG 39

CGA GGC TTT GCC TCG ATT TTC ACC CCC GGG CCA AAG CAG 78

AAC TTG CAG CTC ATA AAT 96

(2) INFORMATION FOR SEQ ID NO:46:

(i) SEQUENCE CHARACTERISTICS:
(A) LENGTH: 96 base pairs
(B) TYPE: nucleic acid
(C) STRANDEDNESS: single
(D) TOPOLOGY: linear (vi) ORIGINAL SOURCE:
(A) ORGANISM: homosapiens -continued (C) INDIVIDUAL ISOLATE: SA13

(xi) SEQUENCE DESCRIPTION: SEQ ID NO:46:

AAC ACC CGC ACT GTG GGT GGT AGT GCG GCC CAA GGC GCG 39

CGC GGG CTC GCT TCA CTT TTC ACC CCT GGG CCG CAG CAG 78

AAC TTG CAG CTC ATA AAT 96

(2) INFORMATION FOR SEQ ID NO:47:

(i) SEQUENCE CHARACTERISTICS:
(A) LENGTH: 96 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: SA4

(xi) SEQUENCE DESCRIPTION: SEQ ID NO:47:

AAC ACC CAC ATT TCG GGC GGT ACT GCT GCT AAA ACT GTG 39

CAA GGT TTT ACT TCA CTT TTC TCC TTC GGG GCA CAG CAG 78

AAT TTG CAG CTC ATA AAT 96

(2) INFORMATION FOR SEQ ID NO:48:

(i) SEQUENCE CHARACTERISTICS:
(A) LENGTH: 96 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: SA7

(xi) SEQUENCE DESCRIPTION: SEQ ID NO:48:

AAC ACT CAC GTT GTG GGC GGT GCC GCT GCT CGT AGT GCG 39

AGT GGC ATG GCC TCA CTC TTT ACT GTC GGG GCA AAG CAG 78

AAT TTG CAG CTC ATA AAT 96

(2) INFORMATION FOR SEQ ID NO:49:

(i) SEQUENCE CHARACTERISTICS:
(A) LENGTH: 93 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: HK2

(xi) SEQUENCE DESCRIPTION: SEQ ID NO:49:

ACC ACC ACC ACC GGC CAC GCA GTG GGC CGC ACA ACC TCC 39

AGC CTT GCC GGG CTT TTC TCC CCC GGT GCC AAG CAA AAT 78

CTA CAA CTT ATC AAC 93

(2) INFORMATION FOR SEQ ID NO:50:

(i) SEQUENCE CHARACTERISTICS:
(A) LENGTH: 32 amino acids
(B) TYPE: amino acid

-continued (C) STRANDEDNESS: unknown
(D) TOPOLOGY: unknown (vi) ORIGINAL SOURCE:
(A) ORGANISM: homosapiens
(C) INDIVIDUAL ISOLATE: S18

(xi) SEQUENCE DESCRIPTION: SEQ ID NO:50:

```
Asp Thr Tyr Ala Thr Gly Gly Ser Ala Ser Arg Thr
  1               5                  10

Thr Gln Ala Phe Thr Arg Phe Phe Ser Pro Gly Ala
         15                  20

Lys Gln Asp Ile Gln Leu Ile Asn
 25                  30
```

(2) INFORMATION FOR SEQ ID NO:51:

(i) SEQUENCE CHARACTERISTICS:
(A) LENGTH: 32 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: S14

(xi) SEQUENCE DESCRIPTION: SEQ ID NO:51:

```
Asp Thr Tyr Ile Thr Gly Gly Thr Ala Gly Arg Thr
  1               5                  10

Val Gly Thr Leu Ser Asn Leu Leu Ala Pro Gly Ala
         15                  20

Lys Gln Asn Ile Gln Leu Ile Asn
 25                  30
```

(2) INFORMATION FOR SEQ ID NO:52:

(i) SEQUENCE CHARACTERISTICS:
(A) LENGTH: 32 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: DK7

(xi) SEQUENCE DESCRIPTION: SEQ ID NO:52:

```
Ser Thr His Val Thr Gly Gly Thr Ala Ala Arg Ala
  1               5                  10

Ala Phe Gly Ile Thr Ser Leu Phe Ala Pro Gly Ala
         15                  20

Lys Gln Asn Ile Gln Leu Ile Ser
 25                  30
```

(2) INFORMATION FOR SEQ ID NO:53:

(i) SEQUENCE CHARACTERISTICS:
(A) LENGTH: 32 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: US11

-continued (xi) SEQUENCE DESCRIPTION: SEQ ID NO:53:

Glu Thr Tyr Val Thr Gly Gly Ser Ala Gly His Ala
1 5 10

Ala Ser Gly Leu Ala Gly Leu Phe Ser Gln Gly Ala
15 20

Gln Gln Asn Ile Gln Leu Ile Asn
25 30

(2) INFORMATION FOR SEQ ID NO:54:

(i) SEQUENCE CHARACTERISTICS:
(A) LENGTH: 32 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: SW1

(xi) SEQUENCE DESCRIPTION: SEQ ID NO:54:

Glu Thr Tyr Thr Thr Gly Gly Ala Ala Gly Gln Thr
1 5 10

Ala Ser Gly Phe Thr Ser Leu Phe Thr Arg Gly Ala
15 20

Gln Gln Asn Ile Gln Leu Val Asn
25 30

(2) INFORMATION FOR SEQ ID NO:55:

(i) SEQUENCE CHARACTERISTICS:
(A) LENGTH: 32 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: DK9

(xi) SEQUENCE DESCRIPTION: SEQ ID NO:55:

Asp Thr Arg Val Thr Gly Gly Ser Ala Ala Arg Asn
1 5 10

Thr Tyr Gly Leu Ala Ser Leu Leu Ser Pro Gly Ala
15 20

Lys Gln Asn Ile Gln Leu Ile Asn
25 30

(2) INFORMATION FOR SEQ ID NO:56:

(i) SEQUENCE CHARACTERISTICS:
(A) LENGTH: 32 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: DR4

(xi) SEQUENCE DESCRIPTION: SEQ ID NO:56:

Gly Thr Gln Val Ser Gly Gly Ser Ala Ala Arg Thr
1 5 10

Val Asn Ala Leu Ala Gly Leu Phe Asp Gln Gly Ala
15 20

-continued

```
Arg Gln Asn Ile Gln Leu Ile Asn
 25                 30


(2) INFORMATION FOR SEQ ID NO:57:

     (i) SEQUENCE CHARACTERISTICS:
          (A) LENGTH:  32 amino acids
          (B) TYPE:  amino acid
          (C) STRANDEDNESS:  unknown
          (D) TOPOLOGY:  unknown

    (vi) ORIGINAL SOURCE:
          (A) ORGANISM:  homosapiens
          (C) INDIVIDUAL ISOLATE:  DR1

    (xi) SEQUENCE DESCRIPTION: SEQ ID NO:57:

Thr Thr His Val Thr Gly Gly Ser Glu Ala Arg Ala
  1               5                  10

Ala Ser Ala Leu Thr Gly Leu Phe Thr Arg Gly Ala
         15                  20

Arg Gln Asn Val Gln Leu Ile Asn
 25                 30


(2) INFORMATION FOR SEQ ID NO:58:

     (i) SEQUENCE CHARACTERISTICS:
          (A) LENGTH:  36 amino acids
          (B) TYPE:  amino acid
          (C) STRANDEDNESS:  unknown
          (D) TOPOLOGY:  unknown

    (vi) ORIGINAL SOURCE:
          (A) ORGANISM:  homosapiens
          (C) INDIVIDUAL ISOLATE:  D3

    (xi) SEQUENCE DESCRIPTION: SEQ ID NO:58:

Arg Gly Gly Val Gly Thr His Thr Ile Gly Gly Ala
  1               5                  10

Gln Ala Tyr Ser Val Arg Gly Phe Thr Ser Ile Phe
         15                  20

Ser Thr Gly Pro Ala Gln Lys Ile Gln Leu Val Asn
 25                 30                  35


(2) INFORMATION FOR SEQ ID NO:59:

     (i) SEQUENCE CHARACTERISTICS:
          (A) LENGTH:  36 amino acids
          (B) TYPE:  amino acid
          (C) STRANDEDNESS:  unknown
          (D) TOPOLOGY:  unknown

    (vi) ORIGINAL SOURCE:
          (A) ORGANISM:  homosapiens
          (C) INDIVIDUAL ISOLATE:  D1

    (xi) SEQUENCE DESCRIPTION: SEQ ID NO:59:

Ser Ala Ser Pro Gly Thr Arg Thr Ile Gly Gly Ser
  1               5                  10

Gln Ala Lys His Thr Ser Ser Ile Val Ser Met Phe
         15                  20

Ser Leu Gly Pro Ser Gln Lys Ile Gln Leu Val Asn
 25                 30                  35


(2) INFORMATION FOR SEQ ID NO:60:
```

-continued (i) SEQUENCE CHARACTERISTICS:
(A) LENGTH: 32 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: P10

(xi) SEQUENCE DESCRIPTION: SEQ ID NO:60:

Arg Thr His Thr Thr Gly Gly Ser Val Ala Tyr Gly
1 5 10

Thr Arg Arg Phe Thr Ser Leu Phe Thr Ser Gly Ala
15 20

Ser Gln Lys Ile Gln Leu Val Asn
25 30

(2) INFORMATION FOR SEQ ID NO:61:

(i) SEQUENCE CHARACTERISTICS:
(A) LENGTH: 32 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: T10

(xi) SEQUENCE DESCRIPTION: SEQ ID NO:61:

Ser Thr Arg Val Thr Gly Gly Thr Ala Ala Arg Asn
1 5 10

Thr Tyr Gly Leu Ala Ser Ile Phe Ala Pro Gly Ala
15 20

Ser Gln Lys Ile Gln Leu Ile Asn
25 30

(2) INFORMATION FOR SEQ ID NO:62:

(i) SEQUENCE CHARACTERISTICS:
(A) LENGTH: 32 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: HK5

(xi) SEQUENCE DESCRIPTION: SEQ ID NO:62:

Ala Thr His Val Thr Gly Gly Thr Ala Ala His Thr
1 5 10

Thr Arg Gly Leu Thr Ser Leu Phe Ala Pro Gly Pro
15 20

Ser Gln Lys Ile Gln Leu Ile Asn
25 30

(2) INFORMATION FOR SEQ ID NO:63:

(i) SEQUENCE CHARACTERISTICS:
(A) LENGTH: 32 amino acids
(B) TYPE: amino acid
(C) STRANDEDNESS: unknown
(D) TOPOLOGY: unknown (vi) ORIGINAL SOURCE:

-continued (A) ORGANISM: homosapiens
(C) INDIVIDUAL ISOLATE: HK8

(xi) SEQUENCE DESCRIPTION: SEQ ID NO:63:

```
Asp Thr Tyr Val Ser Gly Gly Ala Thr Ala Arg Asn
  1               5                  10

Thr Tyr Gly Leu Thr Ser Leu Phe Thr Pro Gly Ala
         15                  20

Ala Gln Lys Ile Gln Leu Ile Asn
 25                  30
```

(2) INFORMATION FOR SEQ ID NO:64:

(i) SEQUENCE CHARACTERISTICS:
(A) LENGTH: 32 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: T3

(xi) SEQUENCE DESCRIPTION: SEQ ID NO:64:

```
Thr Thr His Val Ser Gly Gly Val Ser Ala Arg Thr
  1               5                  10

Thr His Gly Leu Ala Ser Phe Phe Ser Pro Gly Pro
         15                  20

Ser Gln Lys Ile Gln Leu Val Asn
 25                  30
```

(2) INFORMATION FOR SEQ ID NO:65:

(i) SEQUENCE CHARACTERISTICS:
(A) LENGTH: 32 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: SW2

(xi) SEQUENCE DESCRIPTION: SEQ ID NO:65:

```
Asn Thr Tyr Thr Thr Gly Gly Glu Ala Ala Tyr Asn
  1               5                  10

Thr Arg Gly Phe Ala Ser Ile Phe Ser Ser Gly Pro
         15                  20

Ser Gln Lys Ile Gln Leu Val Asn
 25                  30
```

(2) INFORMATION FOR SEQ ID NO:66:

(i) SEQUENCE CHARACTERISTICS:
(A) LENGTH: 32 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: SA10

(xi) SEQUENCE DESCRIPTION: SEQ ID NO:66:

```
Gly Thr Tyr Thr Thr Gly Gly Ala Gln Gly Arg Thr
  1               5                  10
```

```
Thr Ser Ser Phe Val Gly Leu Phe Thr Pro Gly Pro
        15                  20

Ser Gln Arg Ile Gln Leu Val Asn
 25                 30
```

(2) INFORMATION FOR SEQ ID NO:67:

(i) SEQUENCE CHARACTERISTICS:
(A) LENGTH: 32 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: US6

(xi) SEQUENCE DESCRIPTION: SEQ ID NO:67:

```
Glu Thr His Val Thr Gly Gly Ala Gln Ala Tyr Ala
  1               5                  10

Ala Arg Ser Phe Thr Ser Leu Phe Thr Pro Gly Ser
        15                  20

Arg Gln Asn Ile Gln Leu Ile Asn
 25                 30
```

(2) INFORMATION FOR SEQ ID NO:68:

(i) SEQUENCE CHARACTERISTICS:
(A) LENGTH: 32 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: IND5

(xi) SEQUENCE DESCRIPTION: SEQ ID NO:68:

```
Gln Ala Lys Thr Ile Gly Gly Arg Gln Ala His Thr
  1               5                  10

Thr Gly Arg Leu Val Ser Met Phe Thr Pro Gly Pro
        15                  20

Ser Gln Asn Ile Gln Leu Val Asn
 25                 30
```

(2) INFORMATION FOR SEQ ID NO:69:

(i) SEQUENCE CHARACTERISTICS:
(A) LENGTH: 32 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: IND8

(xi) SEQUENCE DESCRIPTION: SEQ ID NO:69:

```
His Thr Asn Ile Ile Gly Gly Arg Glu Ala Ser Thr
  1               5                  10

Thr Gln Gly Phe Thr Ser Leu Phe Ser Pro Gly Ala
        15                  20

Ser Gln Lys Ile Gln Leu Val Asn
 25                 30
```

-continued (2) INFORMATION FOR SEQ ID NO:70:

(i) SEQUENCE CHARACTERISTICS:
(A) LENGTH: 32 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: HK3

(xi) SEQUENCE DESCRIPTION: SEQ ID NO:70:

```
Ser Thr His Thr Ile Gly Ala Thr Val Ala Arg Thr
  1             5                  10

Thr Gln Ser Trp Thr Gly Phe Phe Ser Ser Gly Pro
         15                  20

Ser Gln Lys Ile Gln Leu Ile Asn
 25                  30
```

(2) INFORMATION FOR SEQ ID NO:71:

(i) SEQUENCE CHARACTERISTICS:
(A) LENGTH: 32 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: S9

(xi) SEQUENCE DESCRIPTION: SEQ ID NO:71:

```
Gly Thr Thr Val Thr Gly Ala Val Gln Gly Arg Ser
  1             5                  10

Leu Gln Gly Leu Thr Gly Leu Phe Ser Ser Gly Pro
         15                  20

Thr Gln Lys Leu Gln Leu Val Asn
 25                  30
```

(2) INFORMATION FOR SEQ ID NO:72:

(i) SEQUENCE CHARACTERISTICS:
(A) LENGTH: 32 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: HK4

(xi) SEQUENCE DESCRIPTION: SEQ ID NO:72:

```
Asn Thr Tyr Val Thr Gly Gly Ala Ala Ser His Ser
  1             5                  10

Thr Arg Gly Leu Thr Ser Leu Phe Thr Thr Gly Ala
         15                  20

Ser Gln Lys Ile Gln Leu Ile Asn
 25                  30
```

(2) INFORMATION FOR SEQ ID NO:73:

(i) SEQUENCE CHARACTERISTICS:
(A) LENGTH: 32 amino acids
(B) TYPE: amino acid
(C) STRANDEDNESS: unknown -continued (D) TOPOLOGY: unknown (vi) ORIGINAL SOURCE:
(A) ORGANISM: homosapiens
(C) INDIVIDUAL ISOLATE: S45

(xi) SEQUENCE DESCRIPTION: SEQ ID NO:73:

```
Gly Thr Tyr Thr Ser Gly Gln Ala Ala Gly Arg Thr
  1               5                  10

Thr Ala Gly Phe Thr Ser Ile Phe Asn Pro Gly Ser
         15                  20

Ala Gln Ser Ile Gln Leu Ile Asn
 25                  30
```

(2) INFORMATION FOR SEQ ID NO:74:

(i) SEQUENCE CHARACTERISTICS:
(A) LENGTH: 32 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: DK1

(xi) SEQUENCE DESCRIPTION: SEQ ID NO:74:

```
Thr Thr His Val Thr Gly Ala Val Gln Gly Arg Thr
  1               5                  10

Thr Gln Gly Phe Ala Ser Leu Phe Ser Pro Gly Ser
         15                  20

Ala Gln Lys Ile Gln Leu Val Asn
 25                  30
```

(2) INFORMATION FOR SEQ ID NO:75:

(i) SEQUENCE CHARACTERISTICS:
(A) LENGTH: 32 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: US10

(xi) SEQUENCE DESCRIPTION: SEQ ID NO:75:

```
Ala Thr Arg Thr Val Gly His Ser Ala Ala Tyr Thr
  1               5                  10

Ala Ser Thr Phe Ala Gly Ile Phe Asn Ala Gly Ser
         15                  20

Arg Gln Asn Ile Gln Leu Ile Asn
 25                  30
```

(2) INFORMATION FOR SEQ ID NO:76:

(i) SEQUENCE CHARACTERISTICS:
(A) LENGTH: 32 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: T4

(xi) SEQUENCE DESCRIPTION: SEQ ID NO:76:

-continued

```
Ser Ser Thr Thr Ile Gly Ser Ala Val Ala Ser Thr
  1               5                  10

Thr Arg Gly Leu Thr Gly Leu Phe Ser Pro Gly Ser
         15                  20

Gln Gln Asn Ile Gln Leu Ile Asn
 25                  30
```

(2) INFORMATION FOR SEQ ID NO:77:

(i) SEQUENCE CHARACTERISTICS:
(A) LENGTH: 32 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: T9

(xi) SEQUENCE DESCRIPTION: SEQ ID NO:77:

```
Thr Thr His Thr Ser Gly Gly Thr Ala Gly His Thr
  1               5                  10

Ala Tyr Gly Leu Thr Ser Ile Phe Ser Pro Gly Ala
         15                  20

Arg Gln Lys Ile Gln Leu Ile Tyr
 25                  30
```

(2) INFORMATION FOR SEQ ID NO:78:

(i) SEQUENCE CHARACTERISTICS:
(A) LENGTH: 32 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: T2

(xi) SEQUENCE DESCRIPTION: SEQ ID NO:78:

```
His Thr Glu Leu Thr Gly Ser Asn Ala Gly Arg Thr
  1               5                  10

Thr Gln Gly Leu Ala Ala Phe Phe Thr Pro Gly Ala
         15                  20

Ser Gln Arg Val Gln Leu Ile Asn
 25                  30
```

(2) INFORMATION FOR SEQ ID NO:79:

(i) SEQUENCE CHARACTERISTICS:
(A) LENGTH: 32 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: T8

(xi) SEQUENCE DESCRIPTION: SEQ ID NO:79:

```
Thr Thr Tyr Thr Thr Gly Ala Gln Val Ala Arg Thr
  1               5                  10

Thr Ala Ser Leu Ala Gly Leu Phe Thr Thr Gly Pro
         15                  20
```

-continued

```
Gln Gln Lys Ile Asn Leu Ile Asn
 25                  30
```

(2) INFORMATION FOR SEQ ID NO:80:

(i) SEQUENCE CHARACTERISTICS:
(A) LENGTH: 32 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: DK8

(xi) SEQUENCE DESCRIPTION: SEQ ID NO:80:

```
Ala Thr Tyr Thr Thr Gly Gly Gln Ala Ala Arg Asp
  1               5                  10

Thr Trp Gly Leu Ala Arg Leu Phe Ser Pro Gly Ala
         15                  20

Gln Gln Lys Leu Ser Leu Ile Asn
 25                  30
```

(2) INFORMATION FOR SEQ ID NO:81:

(i) SEQUENCE CHARACTERISTICS:
(A) LENGTH: 32 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: DK11

(xi) SEQUENCE DESCRIPTION: SEQ ID NO:81:

```
Asn Thr Arg Val Thr Gly Ala Ile Ala Gly Arg Thr
  1               5                  10

Ala Ala Ser Leu Ala Ser Leu Phe Asn Ser Gly Pro
         15                  20

Gln Gln Lys Ile Asn Leu Ile Asn
 25                  30
```

(2) INFORMATION FOR SEQ ID NO:82:

(i) SEQUENCE CHARACTERISTICS:
(A) LENGTH: 32 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: S83

(xi) SEQUENCE DESCRIPTION: SEQ ID NO:82:

```
Thr Thr Tyr Thr Thr Gly Ala Ser Ala Gly Gln Gln
  1               5                  10

Val Gln Ser Phe Ala Arg Leu Phe Ser Pro Gly Pro
         15                  20

Asn Gln His Val Gln Leu Val Arg
 25                  30
```

(2) INFORMATION FOR SEQ ID NO:83:

(i) SEQUENCE CHARACTERISTICS:

-continued (A) LENGTH: 32 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: HK10

(xi) SEQUENCE DESCRIPTION: SEQ ID NO:83:

```
Gly Thr Tyr Ile Ser Gly Gly His Val Ala Arg Gly
  1               5                  10

Ala Ser Gly Leu Ala Ser Phe Phe Ser Pro Gly Ala
         15                  20

Lys Gln Asn Leu Gln Leu Ile Asn
 25                  30
```

(2) INFORMATION FOR SEQ ID NO:84:

(i) SEQUENCE CHARACTERISTICS:
(A) LENGTH: 32 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: S2

(xi) SEQUENCE DESCRIPTION: SEQ ID NO:84:

```
Glu Thr Tyr Val Thr Gly Gly Ser Ala Ala Arg Ser
  1               5                  10

Ala Ser Arg Leu Ala Ser Phe Phe Ser Pro Gly Ala
         15                  20

Gln Gln Lys Leu Gln Leu Val Asn
 25                  30
```

(2) INFORMATION FOR SEQ ID NO:85:

(i) SEQUENCE CHARACTERISTICS:
(A) LENGTH: 32 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: S52

(xi) SEQUENCE DESCRIPTION: SEQ ID NO:85:

```
Glu Thr Tyr Val Thr Gly Gly Ser Val Ala His Ser
  1               5                  10

Ala Arg Gly Leu Thr Ser Leu Phe Ser Met Gly Ala
         15                  20

Lys Gln Lys Leu Gln Leu Val Asn
 25                  30
```

(2) INFORMATION FOR SEQ ID NO:86:

(i) SEQUENCE CHARACTERISTICS:
(A) LENGTH: 32 amino acids
(B) TYPE: amino acid
(C) STRANDEDNESS: unknown
(D) TOPOLOGY: unknown (vi) ORIGINAL SOURCE:
(A) ORGANISM: homosapiens -continued (C) INDIVIDUAL ISOLATE: S54

(xi) SEQUENCE DESCRIPTION: SEQ ID NO:86:

```
Ala Thr Tyr Thr Thr Gly Gly Ser Ala Ala His Ser
  1               5                  10

Ala Gln Gly Ile Thr Arg Leu Phe Ser Val Gly Ala
         15                  20

Lys Gln Asn Leu Gln Leu Val Asn
 25                  30
```

(2) INFORMATION FOR SEQ ID NO:87:

(i) SEQUENCE CHARACTERISTICS:
(A) LENGTH: 32 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: DK12

(xi) SEQUENCE DESCRIPTION: SEQ ID NO:87:

```
Thr Thr His Val Thr Gly Gly Asp Ala Ala Arg Ser
  1               5                  10

Thr Leu Arg Phe Thr Ser Leu Phe Ser Val Gly Ser
         15                  20

Asn Gln Gln Leu Gln Leu Val Asn
 25                  30
```

(2) INFORMATION FOR SEQ ID NO:88:

(i) SEQUENCE CHARACTERISTICS:
(A) LENGTH: 32 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: Z4

(xi) SEQUENCE DESCRIPTION: SEQ ID NO:88:

```
His Thr Ser Val Ser Gly Gly Thr Gln Ala Arg Ala
  1               5                  10

Ala Gln Gly Leu Thr Ser Leu Phe Thr Ser Gly Pro
         15                  20

Arg Gln Asn Leu Gln Leu Ile Asn
 25                  30
```

(2) INFORMATION FOR SEQ ID NO:89:

(i) SEQUENCE CHARACTERISTICS:
(A) LENGTH: 32 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: Z1

(xi) SEQUENCE DESCRIPTION: SEQ ID NO:89:

```
Thr Thr Tyr Ala Ser Gly Ala Ala Ala Gly Arg Thr
  1               5                  10
```

-continued

Thr Ser Gly Phe Ala Gly Leu Phe Thr Pro Gly Ala
15 20

Lys Gln Asn Ile Arg Leu Ile Asn
25 30

(2) INFORMATION FOR SEQ ID NO:90:

(i) SEQUENCE CHARACTERISTICS:
(A) LENGTH: 32 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: Z7

(xi) SEQUENCE DESCRIPTION: SEQ ID NO:90:

Thr Thr Met Thr Thr Gly Gly Ala Ala Ala Arg Thr
1 5 10

Ala His Ala Phe Thr Gly Leu Phe Thr Ser Gly Pro
15 20

Gln Gln Lys Leu Gln Leu Ile Asn
25 30

(2) INFORMATION FOR SEQ ID NO:91:

(i) SEQUENCE CHARACTERISTICS:
(A) LENGTH: 32 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: Z6

(xi) SEQUENCE DESCRIPTION: SEQ ID NO:91:

Glu Thr Val Thr Thr Gly Gly Ser Val Ala Arg Ser
1 5 10

Thr Arg Ala Ile Thr Ser Leu Phe Asn Ser Gly Pro
15 20

Lys Gln Asn Leu Gln Leu Ile Asn
25 30

(2) INFORMATION FOR SEQ ID NO:92:

(i) SEQUENCE CHARACTERISTICS:
(A) LENGTH: 32 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: DK13

(xi) SEQUENCE DESCRIPTION: SEQ ID NO:92:

Gly Thr Tyr Val Thr Gly Gly Gln Ala Gly Gln Thr
1 5 10

Ala Phe His Leu Thr Gly Leu Phe Thr Arg Gly Ser
15 20

His Gln Asn Ile Gln Leu Ile Asn
25 30

-continued (2) INFORMATION FOR SEQ ID NO:93:

(i) SEQUENCE CHARACTERISTICS:
(A) LENGTH: 32 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: SA6

(xi) SEQUENCE DESCRIPTION: SEQ ID NO:93:

```
Ser Thr His Ser Val Gly Gly Ser Ala Ala His Thr
  1               5                  10

Thr Ser Gly Phe Thr Ser Leu Phe Asn Pro Gly Pro
         15                  20

Lys Gln Asn Leu Gln Leu Ile Tyr
 25                  30
```

(2) INFORMATION FOR SEQ ID NO:94:

(i) SEQUENCE CHARACTERISTICS:
(A) LENGTH: 32 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: SA1

(xi) SEQUENCE DESCRIPTION: SEQ ID NO:94:

```
Arg Thr His Thr Val Ala Gly Thr Ala Ala Tyr Ser
  1               5                  10

Thr Arg Gly Phe Ala Ser Ile Phe Thr Pro Gly Pro
         15                  20

Lys Gln Asn Leu Gln Leu Ile Asn
 25                  30
```

(2) INFORMATION FOR SEQ ID NO:95:

(i) SEQUENCE CHARACTERISTICS:
(A) LENGTH: 32 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: SA13

(xi) SEQUENCE DESCRIPTION: SEQ ID NO:95:

```
Asn Thr Arg Thr Val Gly Gly Ser Ala Ala Gln Gly
  1               5                  10

Ala Arg Gly Leu Ala Ser Leu Phe Thr Pro Gly Pro
         15                  20

Gln Gln Asn Leu Gln Leu Ile Asn
 25                  30
```

(2) INFORMATION FOR SEQ ID NO:96:

(i) SEQUENCE CHARACTERISTICS:
(A) LENGTH: 32 amino acids
(B) TYPE: amino acid
(C) STRANDEDNESS: unknown
(D) TOPOLOGY: unknown -continued

```
    (vi) ORIGINAL SOURCE:
          (A) ORGANISM:  homosapiens
          (C) INDIVIDUAL ISOLATE:  SA4

    (xi) SEQUENCE DESCRIPTION: SEQ ID NO:96:

Asn Thr His Ile Ser Gly Gly Thr Ala Ala Lys Thr
  1               5                  10

Val Gln Gly Phe Thr Ser Leu Phe Ser Phe Gly Ala
        15                  20

Gln Gln Asn Leu Gln Leu Ile Asn
 25                  30


(2) INFORMATION FOR SEQ ID NO:97:

     (i) SEQUENCE CHARACTERISTICS:
          (A) LENGTH:  32 amino acids
          (B) TYPE:  amino acid
          (C) STRANDEDNESS:  unknown
          (D) TOPOLOGY:  unknown

    (vi) ORIGINAL SOURCE:
          (A) ORGANISM:  homosapiens
          (C) INDIVIDUAL ISOLATE:  SA7

    (xi) SEQUENCE DESCRIPTION: SEQ ID NO:97:

Asn Thr His Val Val Gly Gly Ala Ala Ala Arg Ser
  1               5                  10

Ala Ser Gly Met Ala Ser Leu Phe Thr Val Gly Ala
        15                  20

Lys Gln Asn Leu Gln Leu Ile Asn
 25                  30


(2) INFORMATION FOR SEQ ID NO:98:

     (i) SEQUENCE CHARACTERISTICS:
          (A) LENGTH:  31 amino acids
          (B) TYPE:  amino acid
          (C) STRANDEDNESS:  unknown
          (D) TOPOLOGY:  unknown

    (vi) ORIGINAL SOURCE:
          (A) ORGANISM:  homosapiens
          (C) INDIVIDUAL ISOLATE:  HK2

    (xi) SEQUENCE DESCRIPTION: SEQ ID NO:98:

Thr Thr Thr Thr Gly His Ala Val Gly Arg Thr Thr
  1               5                  10

Ser Ser Leu Ala Gly Leu Phe Ser Pro Gly Ala Lys
        15                  20

Gln Asn Leu Gln Leu Ile Asn
 25                  30
```